US011977075B2

(12) United States Patent
Shaked

(10) Patent No.: US 11,977,075 B2
(45) Date of Patent: *May 7, 2024

(54) METHOD OF PREDICTING PERSONALIZED RESPONSE TO CANCER TREATMENT WITH IMMUNE CHECKPOINT INHIBITORS, METHOD OF TREATING CANCER, AND KIT THEREFOR

(71) Applicant: Rappaport Family Institute for Research in the Medical Sciences, Haifa (IL)

(72) Inventor: Yuval Shaked, Binyamina (IL)

(73) Assignee: Rappaport Family Institute for Research in the Medical Sciences, Haifa (IL)

( * ) Notice: Subject to any disclaimer, the term of this patent is extended or adjusted under 35 U.S.C. 154(b) by 396 days.

This patent is subject to a terminal disclaimer.

(21) Appl. No.: 16/219,203

(22) Filed: Dec. 13, 2018

(65) Prior Publication Data

US 2019/0113513 A1   Apr. 18, 2019

Related U.S. Application Data

(63) Continuation-in-part of application No. PCT/IL2018/050609, filed on Jun. 4, 2018.

(60) Provisional application No. 62/594,141, filed on Dec. 4, 2017, provisional application No. 62/564,392, filed on Sep. 28, 2017, provisional application No. 62/514,851, filed on Jun. 4, 2017.

(51) Int. Cl.
| | |
|---|---|
| *G01N 33/574* | (2006.01) |
| *A61P 35/00* | (2006.01) |
| *C07K 16/00* | (2006.01) |
| *C07K 16/24* | (2006.01) |
| *C07K 16/28* | (2006.01) |
| *G01N 33/577* | (2006.01) |
| *G01N 33/68* | (2006.01) |
| *G01N 33/74* | (2006.01) |
| *G06F 17/15* | (2006.01) |
| *G16B 5/00* | (2019.01) |
| *G16B 25/10* | (2019.01) |
| *G16H 50/20* | (2018.01) |
| *G16H 50/30* | (2018.01) |
| *A61K 39/00* | (2006.01) |

(52) U.S. Cl.
CPC ............ *G01N 33/574* (2013.01); *A61P 35/00* (2018.01); *C07K 16/00* (2013.01); *C07K 16/248* (2013.01); *C07K 16/2803* (2013.01); *C07K 16/2818* (2013.01); *C07K 16/2878* (2013.01); *G01N 33/577* (2013.01); *G01N 33/6857* (2013.01); *G01N 33/74* (2013.01); *G06F 17/15* (2013.01); *G16B 5/00* (2019.02); *G16B 25/10* (2019.02); *G16H 50/20* (2018.01); *G16H 50/30* (2018.01); *A61K 2039/505* (2013.01); *G01N 2800/52* (2013.01)

(58) Field of Classification Search
CPC ..................................................... G01N 33/574
USPC ......................................................... 435/6.14
See application file for complete search history.

(56) References Cited

U.S. PATENT DOCUMENTS

| | | | |
|---|---|---|---|
| 5,595,756 | A | 1/1997 | Bally et al. |
| 11,155,814 | B2 | 10/2021 | Shaked et al. |
| 2016/0024585 | A1 | 1/2016 | Nixon et al. |
| 2017/0114125 | A1 | 4/2017 | Sabbadini et al. |

FOREIGN PATENT DOCUMENTS

| | | |
|---|---|---|
| AU | 2016250478 A1 | 11/2016 |
| JP | 2008502326 A | 1/2008 |
| JP | 2011526674 A | 10/2011 |
| JP | 2015512612 A | 4/2015 |
| JP | 2015516806 A | 6/2015 |
| JP | 2016520800 A | 7/2016 |
| JP | 2016535275 A | 11/2016 |
| WO | 2005119260 A2 | 12/2005 |
| WO | 2009032084 A1 | 3/2009 |
| WO | 2012151574 A1 | 11/2012 |
| WO | 2013106765 A1 | 7/2013 |
| WO | 2013148288 A1 | 10/2013 |
| WO | 2016156501 A1 | 10/2016 |
| WO | 2017011907 A1 | 1/2017 |
| WO | 2017024207 A1 | 2/2017 |
| WO | 2017036020 A1 | 3/2017 |
| WO | 2017040960 A1 | 3/2017 |
| WO | 2017132536 A1 | 8/2017 |
| WO | 2017140826 A1 | 8/2017 |
| WO | 2018071824 A1 | 4/2018 |
| WO | 2018104483 A1 | 6/2018 |

(Continued)

OTHER PUBLICATIONS

Rotz et al (Pediatr Blood Cancer, 2017, 64: e26642, 5 pages).*
Lee et al (Blood, 2014, 124(2): 188-195).*
Tockman et al (Cancer Res., 1992, 52:2711s-2718s).*
Sanmamed et al (Clinical Cancer Research, 2014, 20(22): 5697-5707).*
Dronca et al (Journal of Clinical Oncology, 2017, 35 No. 15 suppl, Abstract 11534).*
Sznol et al (Journal of Clinical Oncology, 2013, 31 No. 18 suppl, Abstract CRA9006^).*

(Continued)

*Primary Examiner* — Sean E Aeder
(74) *Attorney, Agent, or Firm* — The Roy Gross Law Firm, LLC; Roy Gross

(57) ABSTRACT

A method and a kit are provided for predicting a favorable or a non-favorable response of a cancer patient to treatment with an immune checkpoint inhibitor by determining in a biological sample obtained from the cancer patient, before and after the treatment, the changes of the levels of factors/biomarkers generated by the cancer patient in response to said treatment, and a method for treatment of a cancer patient with an immune checkpoint inhibitor.

22 Claims, 7 Drawing Sheets

(56) References Cited

FOREIGN PATENT DOCUMENTS

| WO | 2018222711 A2 | 12/2018 |
|----|---------------|---------|
| WO | 2018225062 A1 | 12/2018 |
| WO | 2018225063 A1 | 12/2018 |

OTHER PUBLICATIONS

Tian et al (Signal Transduction and Targeted Therapy, 2016, 1 (16025), 10 pages).*
Karachaliou et al (Journal of Clinical Oncology, 2017, 35(15 suppl) Abstract 11504).*
Kindler et al (Oncology, 2017, 35(15 suppl) Abstract 8557).*
Yamazaki et al.; "Cytokine biomarkers to predict antitumor responses to nivolumab suggested in a phase 2 study for advanced melanoma". Cancer science, 108.5: 1pp. 022-1031.(2017).
Anonymous: "FAM83 Proteins Promote Tumorigenesis and Drug Resistance", Cancer Discovery, vol. 2, No. 10, 1 page, 2012. Retrieved Oct. 26, 2021; DOI: 10.1158/2159-8290.CD-RW2012-133.
Merhi et al. "Squamous Cell Carcinomas of the Head and Neck Cancer Response to Programmed Cell Death Protein-1 Targeting and Differential Expression of Immunological Markers: A Case Report", Frontiers in Immunology, vol. 9, Article 1769, pp. 1-10, 2018. Retrieved Oct. 26, 2021; doi: 10.3389/fimmu.2018.01769.
Choudhary et al. "Interleukin-6 role in head and neck squamous cell carcinoma progression" World Journal of Otorhinolaryngology—Head and Neck Surgery, 2, pp. 90-97, 2016. Retrieved Oct. 26, 2021 from: http://dx.doi.org/10.1016/j.wjorl.2016.05.002.
Krishnamurthy et al. "Endothelial Interleukin-6 defines the tumorigenic potential of primary human cancer stem cells" Stem Cells, 32(11): 2845-2857, 2014. Retrieved Oct. 26, 2021; doi:10.1002/stem.1793.
Chen et al. Role of Interleukin-6 in the Radiation Response of Liver Tumors. Int J Radiation Oncol Biol Phys, vol. 84, No. 5, pp. e621-e630, 2012; doi: 10.1016/j.ijrobp.2012.07.2360.
Sheng et al. The Relationship Between Serum Interleukin-6 and the Recurrence of Hepatitis B Virus Related Hepatocellular Carcinoma after Curative Resection; Medicine Baltimore. Jun. 2015; 94(24): e941; doi: 10.1097/MD.0000000000000941.
Skolnick et al. From genes to pro in structure and function:novel applications of computational approaches in the genomic era; Trends Biotechnol. Jan. 2000; 18 (1):34-9. DOI: 10.1016/s0167-7799(99)01398-0.
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue; J. Cell Biol. 111: 2129-2138, 1990; https://doi.org/10.1083/jcb.111.5.2129.
Miosge et al. Comparison of predicted and actual consequences of missense mutations; Proc Natl Acad Sci U S A. 2015; 112(37): E5189-98; https://doi.org/10.1073/pnas.1511585112.
Bork, P. Powers and Pitfalls in Sequence Analysis: the 70% Hurdle; Genome Research, 2000, 10:398-400; DOI: 10.1101/gr.10.4.398.
Warzocha et al., Antisense Strategy: Biological Utility and Prospects in the Treatment of Hematological Malignancies; Leukemia and Lymphoma (1997) vol. 24. pp. 267-281; DOI: 10.3109/10428199709039014.
McKeague et al., Challenges and Opportunities for Small Molecule Aptamer Development; J Nucleic Acids. 2012;2012:748913, Epub Oct. 24, 2012; https://doi.org/10.1155/2012/748913.
Vajdos et al., Comprehensive Functional Maps of the Antigen-binding Site of an Anti-Erb82 Antibody Obtained with Shotgun Scanning Mutagenesis; J Mol Biol. Jul. 5, 2022;320(2):415-28; doi: 10.1016/S0022-2836(02)00264-4.
Brown et al., Tolerance to Single, but Not Multiple, Amino Acid Replacements in Antibody V H CDR2; J Immunol. May 1996; 156(9):3285-91; PMID: 8617951.
Guido et al., Virtual Screening and Its Integration with Modern Drug Design Technologies (Curr Med Chem. 2008; 15 (1): 37-46); doi: 10.2174/092986708783330683.
Clark et al., Discovery and Development of Janus Kinase {JAK) Inhibitors for Inflammatory Diseases; J. Med. Chem., 2014, 57 (12), pp. 5023-5038; https://doi.org/10.1021/jm401490p.
Waiker et al., Imperfect Gold Standards for Kidney Injury Biomarker Evaluation (J Am Soc Nephrol. Jan. 2012; 23 (1): 13-21); DOI: 10.1681/ASN.2010111124.
Brooks, J.D. Translational genornics: The challenge of developing cancer biornarkers; Genome Res. 2012. 22: 183-187, doi: 10.1101/gr.124347.111.
McKean et al., Biomarkers in Precision Cancer Immunotherapy: Promise and Challenges; Am Soc Clin Oncol Educ Book. May 2020;40:e275-e291; DOI: 10.1200/EDBK_280571.
Aberuyi et al, Drug Resistance Biomarkers and Their Clinical Applications in Childhood Acute Lymphoblastic leukemia; Front Oncol. 2019; 9: 1496; doi: 10.3389/fonc.2019.01496.
Sporn et al., Chemoprevention of Cancer, Carcinogenesis, vol. 21 (2000) 525-530; DOI: 10.1093/carcin/21.3.525.
Auerbach et al., Angiogenesis assays: Problems and pitfalls; Cancer and Metasis Reviews, 2000, 19: 167-172, DOI: 10.1023/a:1026574416001.
Gura, T. Systems for Identifying New Drugs are Often Faulty; Science, 1997, 278(5340): 1041-1042, DOI: 10.1126/science.278.5340.1041.
HogenEsch et al., Challenges in Pre-clinical Testing of Anti-cancer Drugs in Cell Culture and Animal Models; J Control Release. Dec. 10, 2012; 164(2): 183-186. DOI: 10.1016/j.jconrel.2012.02.031.
Efferth, Thomas, et al. (2006). "Expression profiling of ATP-binding cassette transporters in childhood T-cell acute lymphoblastic leukemia", Molecular Cancer Therapeutics 2006;5(8). doi:10.1158/1535-7163.MCT-06-0086.
Goncalves, Kevin A., et al. (2016). "Angiogenin Promotes Hematopoietic Regeneration by Dichotomously Regulating Quiescence of Stem and Progenitor Cells", Cell Press 166, 894-906. http://dx.doi.org/10.1016/j.cell.2016.06.042.
Pierard, Laure et al. (2017) "Involvement of Angiogenin in Sunitinib Resistance in Human Renal Cell Carcinoma", The Journal of Urology vol. 197, No. 4S, Supplement. https://doi.org/10.1016/j.juro.2017.02.3352.
Wei, Jin, et al. (2017) "MUC1 induces acquired chemoresistance by upregulating ABCB1 in EGFR-dependent manner", Cell Death and Disease 8, e2980, 13 pages. doi:10.1038/cddis.2017.378.
Winter, Stuart S., (2013) ATP Binding Cassette C1 (ABCC1/MRP1)-mediated drug efflux contributes to disease progression in T-lineage acute lymphoblastic leukemia, Health (Irvine Calf) 5(5A): 41-50. doi:10.4236/health.2013.55A005.
Alishekevitz et al., (2016). Macrophage-Induced Lymphangiogenesis and Metastasis following Paclitaxel Chemotherapy is Regulated by VEGFR3. Cell Reports, 17(5), 1344-1356. http://dx.doi.org/10.1016/j.celrep.2016.09.083.
Chen et al., Intermittent Metronomic Drug Schedule is Essential for Activating Antitumor Innate Immunity and Tumor Xenograft Regression. Neoplasia, 16(1), 84-W27, 2014. DOI 10.1593/neo.131910.
Doloff et al. VEGF Receptor Inhibitors Block the Ability of Metronomically Dosed Cyclophosphamide to Activate Innate Immunity-Induced Tumor Regression. Cancer Research, 72(5), 1103-1115, 2012. doi: 10.1158/0008-5472.CAN-11-3380.
Giesen et al., Highly multiplexed imaging of tumor tissues with subcellular resolution by mass cytometry. Nature Methods, 11(4), 417-422, 2014. doi:10.1038/nmeth.2869.
Gingis-Velitski et al., Host Response to Short-term, Single-Agent Chemotherapy Induces Matrix Metalloproteinase-9 Expression and Accelerates Metastasis in Mice. Cancer Research, 71(22), 6986-6996, 2011. doi: 10.1158/0008-5472.CAN-11-0629.
Hughes et al., Matrigel: A complex protein mixture required for optimal growth of cell culture. Proteomics, 10(9), 1886-1890, 2010. DOI 10.1002/pmic.200900758.
Kruisbeek, A. M. (1992). In Vivo Depletion of CD4- and CD8-Specific T Cells. Current Protocols in Immunology, 1(1), 4.1.1-4.1.5, 2001. DOI: 10.1002/0471142735.im0401s01.
Qiu et al., "Extracting a Cellular Hierarchy from High-dimensional Cytometry Data with SPADE", Nat Biotechnol. ; 29 (10): 886-891, 2011. doi:10.1038/nbt.1991.

(56) References Cited

OTHER PUBLICATIONS

Rachman-Tzemah et al., Blocking Surgically Induced Lysyl Oxidase Activity Reduces the Risk of Lung Metastases, Cell Reports; 19(4): pp. 774-784, (2017). http://dx.doi.org/10.1016/j.celrep.2017.04.005.
Ran et al., "Double nicking by RNA-guided CRISPR Cas9 for enhanced genome editing specificity", Cell. 12; 154(6): 1380-1389, 2013. doi:10.1016/j.cell.2013.08.021.
Ran et al., "Genome engineering using the CRISPR-Cas9 system", Nat Protoc. 8(11): 2281-2308, 2013. doi:10.1038/nprot.2013.143.
Shaked et al., "Antiangiogenic Strategies on Defense: On the Possibility of Blocking Rebounds by the Tumor Vasculature after Chemotherapy", Cancer Res. 67(15): pp. 7055-7058 (2007). doi:10.1158/0008-5472.CAN-07-0905.
Sun et al., "IL-10 and PD-1 cooperate to limit the activity of tumor-specific CD8 + T cells" Cancer Res. 75(8): 1635-1644, 2015. doi:10.1158/0008-5472.CAN-14-3016.
Timaner et al., "Analysis of the Stromal Cellular Components of the Solid Tumor Microenvironment Using Flow Cytometry" Curr Protoc Cell Biol. 70:19 pp. 81-82 (2016). doi: 10.1002/0471143030.cb1918s70.
Juric et al., "MMP-9 inhibition promotes anti-tumor immunity through disruption of biochemical and physical barriers to T-cell trafficking to tumors", PLOS One 13(11), 2018. https://doi.org/10.1371/journal.pone.0207255.
Munoz et al., Highly Efficacious Nontoxic Preclinical Treatment for Advanced Metastatic Breast Cancer Using Combination Oral UFTCyclophosphamide Metronomic Chemotherapy, Cancer Res 2006; 66: (7), 3386-3391, 2006. DOI: 10.1158/0008-5472.CAN-05-4411.
Kruger et al., Antimetastatic Activity of a Novel Mechanism-Based Gelatinase Inhibitor; Cancer Res 2005; 65: (9), 3523-3526, 2005. DOI: 10.1158/0008-5472.CAN-04-3570.
Fujiu et al., "A heart-brain-kidney network controls adaptation to cardiac stress through tissue macrophage activation" Nature Medicine, vol. 23, No. 5, 611-622, 2017. doi:10.1038/nm.4326.
Bonfil et al., "Inhibition of human prostate cancer growth, osteolysis and angiogenesis in a bone metastasis model by a novel mechanism-based selective gelatinase inhibitor", Int. J. Cancer: 118, 2721-2726 (2006). DOI: 10.1002/ijc.21645.
Beyar-Katz et al.;". Bortezomib-induced proinflammatory macrophages as a potential factor limiting anti-tumour efficacy". J Pathol. vol. 239,Issue 3. (2016).
De Henau et al.; "Overcoming resistance to checkpoint blockade therapy by targeting PI3Kgamma in myeloid cells". Nature. 539(7629):pp. 443-447.(2016).
De Palma et al;. "Macrophage regulation of tumor responses to anticancer therapies" Cancer Cell. ,23(3):pp. 277-286. (2013).
Duraiswamy et al.;"Dual blockade of PD-1 and CTLA-4 combined with tumor vaccine effectively restores T-cell rejection function in tumors". Cancer Res. ; 73(12): pp. 3591-3603. (2013).
Gajewski et al.; "Innate and adaptive immune cells in the tumor microenvironment." Nat Immunol. ;14(10):pp. 1014-1022. (2013).
Katz et al.; "Host effects contributing to cancer therapy resistance". Drug Resist Updat. 19:pp. 33-42. (2015).
Kim et al.; "Assaying Cell Cycle Status Using Flow Cytometry". Current protocols in molecular biology. ;111:28 6 pp. 1-11. (2016).
Kim et al.; "Macrophages and mesenchymal stromal cells support survival and proliferation of multiple myeloma cells". British Journal of Haematology. ;158(3): pp. 336-346. (2012).
Kodumudi et al.; "Immune Checkpoint Blockade to Improve Tumor Infiltrating Lymphocytes for Adoptive Cell Therapy". PloS one. 11(4):e0153053.(2016).
Ma et al.; "Anticancer chemotherapy-induced intratumoral recruitment and differentiation of antigen-presenting cells". Immunity. 38(4):pp. 729-741. (2013).
Makkouk et al.; "Cancer immunotherapy and breaking immune tolerance: new approaches to an old challenge". Cancer Res. ;75(1):pp. 5-10. (2015).

Ostrand-Rosenberg et al.; "Myeloid-derived suppressor cells: linking inflammation and cancer". Journal of Immunology. ;182(8):pp. 4499-4506. (2009).
Pardoll . "The blockade of immune checkpoints in cancer immunotherapy". Nature reviews Cancer. ;12(4):pp. 252-264. (2012).
Postow et al.; "Immune Checkpoint Blockade in Cancer Therapy". J Clin Oncol. ;33(17):1pp. 974-982. (2015).
Romano ,et al.; "The therapeutic promise of disrupting the PD-1/PD-L1 immune checkpoint in cancer: unleashing the CD8 T cell mediated anti-tumor activity results in significant, unprecedented clinical efficacy in various solid tumors". J Immunother Cancer. ;3:15. (2015).
Sato et al.; "Interleukin 10 in the tumor microenvironment: a target for anticancer immunotherapy". Immunol Res. ;51 (2-3):pp. 170-182. (2011).
Shaked. "Balancing efficacy of and host immune responses to cancer therapy: the yin and yang effects". Nat Rev Clin Oncol. (2016).
Shaked et al.; "Therapy-induced acute recruitment of circulating endothelial progenitor cells to tumors". Science. ;313 (5794):1 pp. 785-787. (2006).
Shaked et al.; "Rapid chemotherapy-induced acute endothelial progenitor cell mobilization: implications for antiangiogenic drugs as chemosensitizing agents". Cancer Cell. ;14(3):pp. 263-273. (2008).
Sharma et al.;"Primary, Adaptive, and Acquired Resistance to Cancer Immunotherapy". Cell. 168(4):pp. 707-723. (2017).
Swart et al.; "Combination Approaches with Immune-Checkpoint Blockade in Cancer Therapy". Frontiers in Oncology. ;6:233. (2016).
Topalian et al.; "Immune checkpoint blockade: a common denominator approach to Cancer Immunotherapy". Cancer Cell ; 27(4): pp. 450-461. (2015).
Yamazaki et al.; "Cytokine biomarkers to predict antitumor responses to nivolumab suggested in a phase 2 study for advanced melanoma". Cancer science, 108.5:, pp. 1022-1031. (2017).
Hamid et al.; "A prospective phase II trial exploring the association between tumor microenvironment biomarkers and clinical activity of ipilimumab in advanced melanoma". Journal of translational medicine, , 9.1: 204. (2011).
Chen et al.; "Analysis of immune signatures in longitudinal tumor samples yields insight into biomarkers of response and mechanisms of resistance to immune checkpoint blockade". Cancer discovery, CD-15-1545. (2016).
Lin et al. (2017) "The role of IL-7 immunity and cancer." Anticancer Research Mar. 2017, 37 (3) 963-967; DOI: 10.21873/anticanres.11405.
Chen et al. (2015). "Siltuximab (CNTO 328): a promising option for human malignancies". Drug Design, Development and Therapy 2015:9 3455-3458; doi: 10.2147/DDDT.S86438.
Wang et al. (2018). "IL-6 mediates platinum-induced enrichment of ovarian cancer stem cells". JCI Insight. Dec. 6, 2018; 3(23): e 122360; DOI: 10.1172/jci.insight.122360.
Turano et al. (2021). "A potential role of IL-6/IL-6R in the development and management of colon cancer". Membranes 2021, 11, 312; DOI: 10.3390/membranes11050312.
Cohen et al. (2013). "Platinum-resistance in ovarian cancer cells is mediated by IL-6 secretion via the increased expression of its target cIAP-2". J Mol Med (Berl). Mar. 2013; 91 (3): 357-68. Epub Sep. 28, 2012; DOI: 10.1007/s00109-012-0946-4.
Choudhary et al. (2016). "Interleukin-6 role in head and neck squamous cell carcinoma progression" World Journal of Otorhinolaryngology—Head and Neck Surgery, 2016, 2, pp. 90-97. doi: 10.1016/j.wjorl.2016.05.002.
Krishnamurthy et al. (2014). "Endothelial Interleukin-6 defines the tumorigenic potential of primary human cancer stem cells" Stem Cells, 2014, 32(11): 2845-2857.doi:10.1002/stem.1793.
Merhi et al. (2018). "Squamous Cell Carcinomas of the Head and Neck Cancer Response to Programmed Cell Death Protein-1 Targeting and Differential Expression of Immunological Markers: A Case Report", Frontiers in Immunology, 2018, vol. 9, Article 1769, pp. 1-10. doi: 10.3389/fimmu.2018.01769.
Anonymous: "FAM83 Proteins Promote Tumorigenesis and Drug Resistance", Cancer Discovery, 2012, vol. 2, No. 10, 1 page. DOI: 10.1158/2159-8290.CD-RW2012-133.

(56) References Cited

OTHER PUBLICATIONS

Lavi et al., "Sustained delivery of IL-1Ra from biodegradable microspheres reduces the number of murine B16 melanoma lung metastases" Journal of Controlled Release, 123, 2007; 123-130. doi:10.1016/j.jconrel.2007.07.015.

McMichael et al., "IL-21 Enhances Natural Killer Cell Response to Cetuximab-Coated Pancreatic Tumor Cells" Clinical Cancer Research, 2017, 23(2); 489-502. DOI: 10.1158/1078-0432.CCR-16-0004.

Peng et al., "PD-1 Blockade Enhances T-cell Migration to Tumors by Elevating IFN-γ Inducible Chemokines" Cancer Research, 2012, 72(20); 5209-5218. doi:10.1158/0008-5472.CAN-12-1187.

Ragnhammar et al., "Neutralising antibodies to granulocyte-macrophage colony stimulating factor (GM-CSF) in carcinoma patients following GM-CSF combination therapy" 1996, 13; 161-166. DOI: 10.1007/BF02990843.

Bent et al., "A senescence secretory switch mediated by PI3K/AKT/mTOR activation controls chemoprotective endothelial secretory responses" Genes & Development 30:1-11, 2016. doi: 10.1101/gad.284851.116.

Gonnelli et al., "No effect of covalently linked poly(ethylene glycol) chains on protein internal dynamics" Biochimica et Biophysica Acta 1794 (2009) 569-576. DOI: 10.1016/j.bbapap.2008.12.005.

Wei et al., "Analysis of the role of the interleukins in colon cancer" Biological Research, (2020) 53:20, pp. 1-9. https://doi.org/10.1186/s40659-020-00287-2.

InVivoMab anti-mouse IL-7R product sheet (cat. #BE002), downloaded from https://bioxcell.com/invivomab-anti-mouse-il-7ra-cd127 on Aug. 6, 2023. (Year:2023).

Xiao-Yun Li et al., "Doxorubicin resistance induces IL6 activation in the colon cancer cell line LS180" Oncology Letters, 16: 5923-5929, 2018.—pp. 7.

Hirotake, Tsukamoto et al., "Combined Blockade of IL6 and PD-1/PD-L1 Signaling Abrogates Mutual Regulation of Their Immunosuppressive Effects in the Tumor Microenvironment" American Association for Cancer Research, 78(17), Sep. 1, 2018.—pp. 12.

Journal of Military Surgeon in Southwest China, vol. 13, No. 4, 704-707, Jul. 15, 2011.

* cited by examiner

Days post tumor cell injection

Days post tumor cell injection

METHOD OF PREDICTING PERSONALIZED RESPONSE TO CANCER TREATMENT WITH IMMUNE CHECKPOINT INHIBITORS, METHOD OF TREATING CANCER, AND KIT THEREFOR

CROSS-REFERENCE TO RELATED APPLICATIONS

The present application is a continuation-in-part of International Application No. PCT/IL2018/050609, filed Jun. 4, 2018, in which the United States is designated, and is a non-provisional of the Provisional Application No. 62/594,141, filed Dec. 4, 2017, and is a non-provisional of the Provisional Application No. 62/564,392, filed Sep. 28, 2017, and is a non-provisional of the Provisional Application No. 62/514,851, filed Jun. 4, 2017, the entire contents of each and all these applications being hereby incorporated by reference herein in their entirety as if fully disclosed herein.

FIELD OF THE INVENTION

The present invention is in the field of oncology and particularly relates to a method of predicting a personalized response of a cancer patient to treatment with immune checkpoint inhibitors, to kits therefor, and to a method of treatment of a cancer patient with an immune checkpoint inhibitor.

BACKGROUND

One of the major obstacles in clinical oncology is that tumors often develop resistance to therapy even when an initial tumor response to treatment is observed. Many studies have focused on the contribution of mutations and genetic aberrations in the tumor cells which promote drug resistance and can explain tumor re-growth. However, studies have demonstrated that the host, in response to cancer therapy, generates pro-tumorigenic and pro-metastatic effects which in turn contribute to tumor re-growth, and therefore negate the anti-tumor activity of the drug (for reviews see Katz and Shaked, 2015; Shaked, 2016).

Host-mediated responses to anti-cancer treatment modalities may be molecular and/or cellular responses. Upon treatment with chemotherapeutic drugs, host bone marrow derived cells (BMDCs) are mobilized from the bone marrow compartment, colonize the treated tumor and contribute to tumor angiogenesis and cancer re-growth, thereby promoting therapy resistance (Shaked et al., 2006, 2008). Cancer therapy also induces pro-tumorigenic activation of various immune cells such as macrophages and antigen presenting cells (Beyar-Katz et al., 2016; De Palma and Lewis, 2013; Kim et al. 2012; Ma et al., 2013). Overall, these aforementioned studies indicate that host-mediated molecular and cellular responses to different anti-cancer treatments involve the activation or education of immune cells as well as the secretion of various pro-tumorigenic factors. These combined effects contribute to tumor re-growth and resistance to therapy. This relatively new phenomenon has made a paradigm shift in understanding cancer progression and resistance to therapy.

Recently, a new treatment modality, an immunotherapy using immune checkpoint inhibitors (ICIs), is revolutionizing cancer therapy. Such immune-modulating drugs have shown remarkable successes for the treatment of advanced malignancies (including stage IV) such as melanoma, prostate, non-small cell lung cancer, renal cell carcinoma and also some hematological malignancies (Postow et al., 2015). Although the human immune system is capable of recognizing and mounting a response to cancerous cells, this response is often circumvented by tumor-derived inhibition resulting in immune tolerance. In this regard, tumor-infiltrating lymphocytes (TILs), such as tumor antigen-specific $CD8^+$ cytotoxic T lymphocytes (CTLs) and natural killer (NK) cells, have been found to colonize the tumor microenvironment (Gajewski et al., 2013). Yet, at the tumor site, they completely lack the ability to act against tumor cells (Ostrand-Rosenberg and Sinha, 2009). This is due to direct inhibitory effects of factors secreted by cancer cells, stromal cells or other suppressive immune cells such as myeloid derived suppressor cells (MDSCs) and T regulatory cells (Tregs) (Makkouk and Weiner, 2015). For instance, IL-10 is frequently upregulated in various types of cancer, and was shown to suppress the immune system (Sato et al., 2011). Thus, identifying molecules that negatively regulate the immune system against tumor cells, will lead to the development of immunomodulatory drugs that support the activation of immune cells against tumors.

Of specific interest are immune checkpoint proteins, such as CTLA-4, PD-1 and its ligand, PD-L1. These checkpoint proteins are expressed by tumor cells or other immune cells and contribute to the exhaustion of CTLs (Postow et al., 2015; Topalian et al., 2015). Specifically, they keep immune responses in check, and inhibit T cell killing effects against tumor cells. As such, checkpoint inhibitors have been developed in order to inhibit the immune suppression effects. Currently, antibodies blocking the immune checkpoints, CTLA-4 and PD-1 or its ligand PD-L1 have been developed (Pardoll, 2012). These ICIs are currently in use in the clinic for the treatment of various malignancies with some promising and remarkable successes (Romano and Romero, 2015). However, ICIs have shown therapeutic benefit only for a limited portion of cancer patients (~10-20%). For example, pooled data from clinical studies of ipilimumab, a CTLA-4 blocking antibody, revealed that the duration of clinical response is around 3 years, and can last up to 10 years. However, this dramatic therapeutic effect is only observed in a subset of patients (~20%). Thus, the majority of patients exhibit intrinsic resistance mechanisms to such therapies. Yet, the molecular aspects that define the subpopulation of patients that are responsive to ICIs are not fully clear. It has been suggested that markers, such as PD-L1 expression by tumor cells, mutational burden, and lymphocytic infiltrates could predict the cancer patients that will respond to immunotherapy. However, these aforementioned biomarkers do not always correlate with tumor responsiveness to immunotherapy or resistance of patients to ICIs. Therefore, additional possible mechanisms are still unknown.

It would be highly desirable to unveil host-mediated cellular and molecular mechanisms that contribute to tumor resistance to all modalities of cancer therapy including the promising ICI therapy modality. This will permit development of strategies to block such unwanted host effects and will improve therapeutic outcome and delay resistance to cancer therapy.

SUMMARY OF THE INVENTION

In one aspect, the present invention relates to a method for identification of a set of host-driven resistance factors to cancer immunotherapy with one or more immune checkpoint inhibitors (hereinafter "ICIs") in a biological sample of a cancer patient treated with said therapy. These factors are Specific Host-Driven Resistance Factors, namely, they are not generated by intrinsic resistance of the cancer cells, but are driven by the host, i.e., the cancer patient, in response to said cancer therapy using ICIs and may limit or counteract the effectiveness of the treatment with the ICIs applied to said patient. The determination of these factors allows the prediction in a personalized form of the favorable or non-favorable response of the patient to the treatment with the ICIs. These factors, herein designated interchangeably "factors" or "biomarkers", are factors, mainly cytokines, chemokines, growth factors, soluble receptors, enzymes and other molecules produced by the host cells, either at different organs or at the tumor microenvironment, in response to the cancer therapy with the ICI with which the patient is treated.

Thus, in certain embodiments, the present invention provides a method for predicting the response of a cancer patient to treatment with at least one immune checkpoint inhibitor, comprising: determining in a biological sample obtained from the cancer patient at a time period after a session of treatment with said at least one immune checkpoint inhibitor the levels of a plurality of factors generated by the cancer patient in response to said treatment, one or more of the plurality of factors promoting responsiveness or non-responsiveness of the patient to the treatment with the ICI, wherein a change in the levels of two or more of the plurality of factors as compared to a reference level, predicts a favorable or a non-favorable response of the cancer patient to the treatment with said at least one immune checkpoint inhibitor.

In certain embodiments, the biological sample is blood plasma. In certain embodiments, the biological sample of the cancer patient is a whole blood sample. In certain embodiments, the biological sample is blood serum. In certain embodiments, the biological sample is peripheral blood mononuclear cells.

In certain embodiments, the invention provides a method for predicting the response of a cancer patient to treatment with an immune checkpoint inhibitor (ICI), the method comprising the steps of:

(i) performing an assay on a biological sample selected from blood plasma, whole blood, blood serum or peripheral blood mononuclear cells obtained from the cancer patient at a time period after a session of treatment with said ICI, to determine the levels of one or more of a plurality of factors induced in the circulation of said cancer patient in response to treatment with said ICI, said one or more of the plurality of factors promoting responsiveness or non-responsiveness of the cancer patient to the treatment with said ICI;

(ii) obtaining reference levels for each of the one or more of the plurality of the induced factors of step (i) in a biological sample obtained from the cancer patient before said session of treatment with the ICI;

(iii) establishing the fold change for each of the one or more of the plurality of the induced factors of step (i) by comparing the level of each induced factor of step (i) with the reference level of step (ii) for the same factor; and (iv) determining that the cancer patient has a favorable or a non-favorable response to the treatment with said ICI based on the fold change established in step (iii) for one or more of the plurality of induced factors of step (i).

In another aspect, the present invention provides a kit comprising a plurality of antibodies, each antibody of the plurality of antibodies selectively binding to each of a plurality of factors that promote responsiveness or non-responsiveness of a cancer patient to treatment with an immune checkpoint inhibitor, and instructions for use.

In a further aspect, the invention provides a method for treatment of a cancer patient with an immune checkpoint inhibitor.

DETAILED DESCRIPTION

Figure 1A:
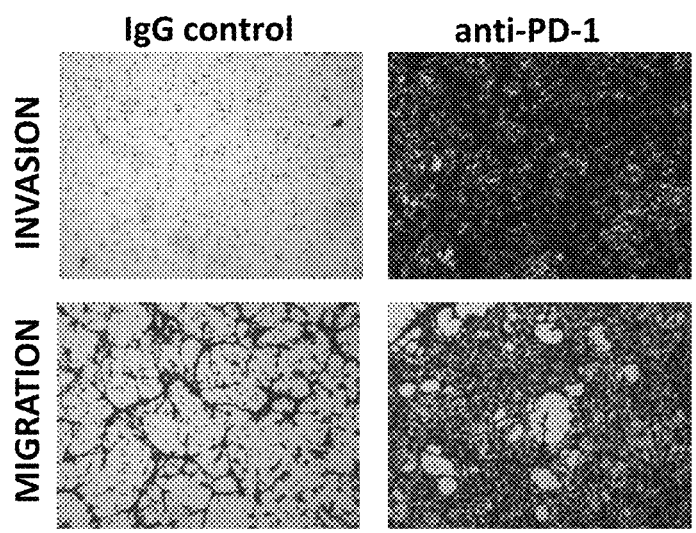
FIG. 1A-D demonstrates that plasma and bone marrow cells derived from anti-PD-1-treated naïve BALB/c mice enhance the metastatic properties of tumor cells. Naïve (non-tumor bearing) 8-10 week old BALB/c mice were treated with anti-PD-1 or control antibodies for 1 week (n=3 mice/group). (A) Invasion and migration properties of EMT6 cells were assessed in a Boyden chamber assay in the presence of plasma extracted from control and anti-PD-1-treated mice. Representative images of invading and migrating cells are shown. (B) Cell coverage was quantified from the images and fold increase in cell coverage was calculated. Averages of 3 biological repeats are shown. (C-D) Bone marrow cells flushed from femurs of control or anti-PD-1-treated mice were cultured in serum-free DMEM for 24 hours ($1 \times 10^6$ cells/ml). Conditioned medium was collected and assessed by zymography to evaluate MMP activity. A representative zymography blot is shown in (C) and quantification of MMP9 is shown in (D). The experiment was performed in three biological repeats. *$p<0.05$; ***$p<0.001$, using Student t-test.

Before describing the methods and kits of the invention, it should be understood that this invention is not limited to the particular methodology and protocols as described herein. It is also to be understood that the terminology used herein is for the purpose of describing particular embodiments of the invention only and, if not defined otherwise, it is not intended to limit the scope of the present invention which will be recited in the appended claims.

It must also be noted that as used herein and in the appended claims, the singular form "a", "an", and "the" include plural reference unless the context clearly dictates otherwise.

As used herein, the term "a cancer therapy" may be used interchangeably with the term "a cancer therapy modality", and include plural reference, namely, one single modality therapy or a combination of two or more modality therapies.

As used herein, the terms "induced", "driven" and "generated" are used interchangeably to denote the factors induced into the circulation by the cancer patient in response to the cancer therapy ("host-response").

In accordance with the present invention, a method is provided for predicting the response of a cancer patient to treatment with at least one immune checkpoint inhibitor (ICI), comprising: determining in a biological sample obtained from the cancer patient at a time period after a session of treatment with said at least one immune checkpoint inhibitor the levels of a plurality of factors generated by the cancer patient in response to said treatment, one or more of the plurality of factors promoting responsiveness or non-responsiveness of the patient to the treatment, wherein a change in the levels of two or more of the plurality of factors, as compared to a reference level, predicts a favorable or a non-favorable response of the cancer patient to the treatment with said at least one immune checkpoint inhibitor.

The biological sample may be whole blood sample, blood plasma, blood serum, or peripheral blood mononuclear cells. In certain embodiments, the biological sample is blood plasma.

In cancer therapy, a cycle of treatment means that the drug is administered to the patient at one point in time (for example, injections over a day or two) and then there is some time (e.g., 1, 2 or 3 weeks) with no treatment. The treatment and rest time make up one treatment cycle. When the patient gets to the end of the cycle, it starts again with the next cycle. A series of cycles of treatment is called a course.

As used herein, "a session of treatment" refers to the "one point in time" when the ICI is administered to the patient at the beginning of a cycle of treatment.

As used herein, the term "an immune checkpoint inhibitor (ICI)" refers to a single ICI, a combination of ICIs and a combination of an ICI with another cancer therapy.

As used herein, the term "treatment" refers to "treatment with an ICI" alone or in combination with another ICI or another cancer therapy.

In certain embodiments, the invention relates to a method for predicting the response of a cancer patient to treatment with an immune checkpoint inhibitor (ICI), the method comprising the steps of:

(i) performing an assay on a biological sample selected from blood plasma, whole blood, blood serum or peripheral blood mononuclear cells obtained from the cancer patient at a time period after a session of treatment with said ICI, to determine the levels of one or more of a plurality of factors induced in the circulation of said cancer patient in response to treatment with said ICI, said one or more of the plurality of factors promoting responsiveness or non-responsiveness of the cancer patient to the treatment with said ICI;

(ii) obtaining reference levels for each of the one or more of the plurality of the induced factors of step (i) in a biological sample obtained from the cancer patient before said session of treatment with the ICI;

(iii) establishing the fold change for each of the one or more of the plurality of the induced factors of step (i) by comparing the level of each induced factor of step (i) with the reference level of step (ii) for the same factor; and (iv) determining that the cancer patient has a favorable or a non-favorable response to the treatment with said ICI based on the fold change established in step (iii) for one or more of the plurality of induced factors of step (i).

In preferred embodiments, both the biological samples of steps (i) and (ii) are blood plasma.

In certain embodiments of the invention, the session of treatment with the ICI is one of multiple sessions of treatment. In certain embodiments, the one of multiple sessions of treatment with the ICI is the first session of treatment with said ICI, the biological sample of step (i) is obtained from the cancer patient at about 20, 24, 30, 36, 40, 48, 50, 60, 72 hours or more, including up to one week or more, up to three weeks or more, after said first session of treatment, and the reference biological sample of step (ii) is obtained from the cancer patient at a time point including at about 72 hours or less, including at about 60, 50, 48, 40, 36, 30, 24 or 20 hours or less or just before said first session of treatment with the ICI.

In certain embodiments, the one of multiple sessions of treatment of the cancer patient with the ICI is the first session of treatment, when the treatment with the ICI is started. In this case, the reference/baseline sample of step (ii), preferably blood plasma, is obtained from the cancer patient at a time point before starting the treatment including at about 72 hours or less, including at about 60, 50, 48, 40, 36, 30, 24 or 20 hours or just before said first session of treatment with the ICI. The comparison is then made between the concentration levels of the factors determined in the biological sample, preferably blood plasma, obtained from the cancer patient at about 20, 24, 30, 36, 40, 48, 50, 60, 72 hours or more, including up to one week or more, up to three weeks or more, after said first session of treatment with the ICI.

In certain other embodiments of the invention, the session of treatment of the cancer patient with the ICI is one of multiple sessions of treatment that is not the first session of treatment with the ICI. In this case, the biological sample is obtained from the cancer patient at any time point between two consecutive sessions of treatment with the ICI and serves simultaneously as the biological sample of step (i) and the reference biological sample according to step (ii) for the next session assay according to step (i). The time between two consecutive sessions of treatment depends on the treatment protocol approved for the specific ICI and may be, for example, of 2 or 3 weeks, depending on the ICI, and the biological sample may be obtained at day 1, 2, 3, 7, 14, or 21 days between two consecutive sessions.

In accordance with the invention, the levels of the plurality of factors generated by the host/cancer patient in response to the treatment with the immune checkpoint inhibitor are determined in the biological sample, preferably blood plasma, obtained from the patient after treatment with ICI. The value (factor concentration in pg/mL) obtained for each factor is then compared with a reference level, which is the baseline level of concentration of the same factor determined in a biological sample, preferably blood plasma, obtained previously from the same cancer patient (hereinafter "reference/baseline sample"). The change in the level of one or more of the factors identified in the biological sample obtained from the cancer patient after the treatment with the ICI compared to the reference/baseline level, is defined by the fold change for each factor. The fold change for each factor is determined by calculating the ratio of treatment:reference/baseline values for the factor.

In certain embodiments, the fold change denotes an increase (up-regulation) of at least 1.5-fold or a decrease (down-regulation) of at least 0.5-fold in the level of each of the one or more of the pro-tumorigenic or pro-metastatic factors generated by the cancer patient in response to the treatment with the ICI. A fold-change of ≥1.5 indicating upregulation or a fold change of ≤0.5 indicating down-regulation in the level of each of the one or more of the plurality of pro-tumorigenic or pro-metastatic factors induced in the circulation of the cancer patient in response to the treatment with the ICI, these values being considered significant and predictive of a non-favorable or favorable response of the cancer patient to the treatment with the said ICI.

The prediction of a favorable or a non-favorable response of the cancer patient to the treatment with the ICI is based on significant fold changes of one or more, optionally two or more, three or more, four or more, five or more, six or more, seven or more, eight or more, nine or more, ten or more, eleven or more, twelve or more, thirteen or more, fourteen or more, fifteen or more, twenty or more, or twenty-five or more, of the induced factors.

The factors/biomarkers induced into the circulation of the cancer patient in response to treatment with the ICI include molecular factors such as cytokines, chemokines, growth factors, enzymes and soluble receptors.

The factors may be pro-tumorigenic or pro-metastatic factors. The pro-tumorigenic factors may be pro-angiogenic, pro-inflammatory/chemotactic or proliferative growth factors.

In accordance with the invention, the change in the level of one or more of the factors/biomarkers identified in the biological sample obtained from the cancer patient after the treatment with the ICI compared to the reference/baseline level, is defined by the fold change for each factor. The fold change for each factor is determined by calculating the ratio of treatment:reference/baseline values for the factor.

In certain embodiments, the change in the level of the factors is an increase (up-regulation) of at least 1.5-fold or a decrease (down-regulation) of at least 0.5-fold in the level of each of the one or more of the factors generated by the cancer patient in response to the treatment with the ICI. A fold change of ≥1.5 indicating upregulation of the factor or a fold change of ≤0.5 indicating down-regulation of the factor are considered significant according to the invention and and predictive of a favorable or a non-favorable response of the cancer patient to the treatment with the ICI.

The change in the level of one or more of the factors/biomarkers identified in the biological sample obtained from the cancer patient after the treatment with ICI compared to the reference/baseline level, if significant, predicts a favorable or a non-favorable response of said cancer patient to said cancer therapy. The fold change is considered significant if it is of at least about 1.5 fold or higher, i.e., ≥1.5 (up-regulation), or if it is at least about 0.5 fold or lower, i.e., ≤0.5 (down-regulation). As used herein, the fold change "considered significant" is predictive of a favorable or a non-favorable response of the cancer patient to said treatment with ICI.

The fold change is determined for all circulating factors in the patient's biological sample. The prediction of a favorable or a non-favorable response of the cancer patient to the treatment will be based on the significant fold changes of one or more, optionally two or more, three or more, four or more, five or more, six or more, seven or more, eight or more, nine or more, ten or more, eleven or more, twelve or more, thirteen or more, fourteen or more, fifteen or more, twenty or more, or twenty-five or more, of the induced factors.

In certain embodiments, the change is an increase (up-regulation) of at least about 1.5 fold in the level of one or more of the biomarkers. If the increase is in the level of biomarkers that are pro-tumorigenic or pro-metastatic, this indicates a non-favorable response of the cancer patient to the treatment.

In certain embodiments, the change is a decrease (down-regulation) of at least about 0.5 fold in the level of one or more of the biomarkers. If the decrease is in the level of biomarkers that are pro-tumorigenic or pro-metastatic, this indicates a favorable response of the cancer patient to the treatment.

In certain embodiments, the session of treatment is the first session of a plurality of sessions of treatment of the cancer patient, when the treatment is started. In this case, the comparison is between the factors determined in the biological sample, preferably blood plasma, obtained from the cancer patient after first starting treatment with the ICI, and the same factors found in the reference/baseline biological sample, preferably blood plasma, obtained from the cancer patient before starting treatment with the ICI. The results may assist the medical oncologists treating the patient to decide if or how to continue the treatment of the cancer patient.

In certain embodiments, the method of the invention is performed for monitoring treatment response in a cancer patient being treated with an ICI. In this case, the session of treatment is one of the sessions of several sessions of treatment, but not the first one. The results will assist the medical oncologist in their decisions if or how to continue the treatment.

In certain embodiments, the fold change determined for pro-tumorigenic factors is predictive of the patient's favorable response to the cancer therapy and the decision may be to continue the treatment with the same ICI as scheduled.

In certain embodiments, the fold change determined for pro-tumorigenic factors is predictive of the patient's non-favorable response to the ICI. In this case, depending on the specific biological activity of the pro-tumorigenic factors, the decision may be to continue the treatment with the same ICI but with the addition of a drug that blocks the biological activity of the tumorigenic factors, for example, by adding to the treatment an anti-inflammatory drug if the factors are pro-inflammatory or by adding to the treatment an anti-angiogenic drug if the factors are pro-angiogenic.

In certain embodiments, the fold change determined for pro-tumorigenic factors is predictive of the patient's non-favorable response to the ICI used and the medical oncologist's decision may be to change the treatment using a different ICI, or to use a combination of two ICIs, or a combination of the ICI with another drug used in cancer therapy.

Immune checkpoints are regulators of immune activation. They play a key role in maintaining immune homeostasis and preventing autoimmunity. In cancer, immune checkpoint mechanisms are often activated to suppress the nascent anti-tumor immune response. Immune checkpoint molecules are considered as good targets for cancer immunotherapy. Immune checkpoint inhibitors (ICI) that cause blockade of the immune checkpoint molecules are considered good candidates for the development of drugs for cancer immunotherapy with the potential for use in multiple types of cancers and are already in use or are under development.

Examples of immune checkpoints that are candidates as targets for development of immune checkpoint inhibitor (ICI) drugs include PD-1 (Programmed Death-1) that has two ligands, PD-L1 and PD-L2; CTLA-4 (Cytotoxic T-Lymphocyte-Associated protein 4); A2AR (Adenosine A2A receptor), also known as ADORA2A; BT-H3, also called CD276; BT-H4, also called VTCN1; BT-H5; BTLA (B and T Lymphocyte Attenuator), also called CD272; IDO (Indoleamine 2,3-dioxygenase); MR (Killer-cell Immunoglobulin-like Receptor); LAG-3 (Lymphocyte Activation Gene-3); TDO (Tryptophan 2,3-dioxygenase); TIM-3 (T-cell Immunoglobulin domain and Mucin domain 3); VISTA (V-domain Ig suppressor of T cell activation).

In certain embodiments of the invention, the ICI is a monoclonal antibody (mAb) against PD-1 or PD-L1 that neutralizes/blocks the PD-1 pathway. In certain embodiments, the anti-PD-1 mAb is Pembrolizumab (Keytruda; formerly called lambrolizumab), approved or tested for treatment of advanced or unresectable melanoma, metastatic non-small cell lung cancer (NSCLC), renal cell carcinoma (RCC), and recurrent squamous cell carcinoma of the head and neck (SCCH). In certain embodiments, the anti-PD-1 mAb is Nivolumab (Opdivo), approved or tested for NSCLC, RCC, melanoma and colorectal cancer (CRC). In certain embodiments, the anti-PD-1 mAb is Pidilizumab (CT0011), approved or tested for non-Hodgkin's lymphoma, chronic lymphocytic leukemia, Hodgkin's lymphoma, multiple myeloma, and acute myeloid leukemia. In certain embodiments, the anti-PD-1 mAb is REGN2810, AMP-224, MEDI0680, or PDR001.

In certain other embodiments of the invention, the immune checkpoint inhibitor is a mAb against PD-L1. In certain embodiments, the anti-PD-L1 mAb is Atezolizumab (Tecentriq), Avelumab (Bavencio), or Durvalumab (Imfinzi), approved for multiple cancers. Atezolizumab is being tested in combination with one or two other cancer agents such as bevacizumab, gemcitabine, cisplatin, docetaxel, paclitaxel, vinflunine entinostat, daratumumab, MPDL3280A, carboplatin, Nab-paclitaxel, Radium-223 dichloride, obinutuzumab, for multiple cancers.

In certain other embodiments of the invention, the ICI is a mAb antibody against CTLA-4. In certain embodiments, the anti-CTLA-4 Ipilimuniab (Yervoy), approved or tested for advanced/metastatic melanoma and castrate-resistant prostate cancer. In certain other embodiments, the anti-CTLA-4 mAb is Tremelimumab (formerly ticilimumab).

In certain embodiments, the ICI is an inhibitor including: (i) anti-B7-H3, such as MGA271; (ii) anti-IDO, such as epacadostat; (iii) anti-KIR, such as Lirilumab; (iv) anti-LAG-3, such as Relatlimab (BMS-986016), LAG 525, REGN3767; (v) anti-TIM-3, such as TSR022 or MBG453; and (vi) anti-VISTA, such as JNJ 61610588.

In certain embodiments, a combination of two ICIs is used according to the invention. In certain embodiments, the combination comprises an anti-PD-1 and an anti-CTLA-4, e.g., Nivolumab-Ipilimumab and REGN2810-Ipilimumab. In certain embodiments, the combination comprises an anti-PD-L1 and an anti-CTLA-4, e.g., Durvalumab-Tremelimumab. In certain embodiments, the combination comprises an anti-PD-1 and an anti-PD-L1, e.g., Nivolumab-Atezolimumab. In certain embodiments, the combination comprises an anti-LAG-3 and an anti-PD-1, e.g., Relatlimab-Nivolumab or REGN3767-REGN2810. In certain embodiments, the combination comprises an anti-PD-1 and an IDO inhibitor, e.g., Pembrolizumab and Epacadostat and Nivolumab-Epacadostat.

Costimulatory molecules such as CD137 (4-1BB), CD134 (OX40), glucocorticoid-induced TNFR (GiTR CD357), and CD40 are expressed by activated T cells, activated natural killer (NK) cells, natural killer T (NKT) cells, Tregs, and other immune cells. The inhibition of the immune checkpoint PD-1 and stimulation of costimulatory molecules by agonist antibodies are complementary strategies to enhance immune responses and therefore provide a strong rationale for use in combination. Thus, in certain embodiments, the invention encompasses a combination of an ICI with an agonistic mAb against T-cell co-stimulatory molecules including an anti-ICOS mAb, e.g., MEDI-570 or BMS-986226: an anti-OX40 mAb e.g., MOXR0916, KHK4083, MEDI0562 or MEDI6469; an anti-CD40 mAb; and an anti-CD137 (4-IBB) mAb, e.g., Urelumab or Utomilumab.

In certain embodiments of the invention, the ICI is administered in combination with one or more conventional cancer therapy including chemotherapy, targeted cancer therapy and radiotherapy. Combinations of ICI and radiation therapy have been studied in multiple clinical trials.

In certain embodiments, the ICI is used in combination chemotherapy that may be with a single or a combination of chemotherapy drugs, or metronomic chemotherapy. The combinations Pembrolizumab+carboplatin+paclitaxel, Pembrolizumab+gemcitabine+docetaxel, Nivolumab+gemcitabine+cisplatin, Ipilimumab+carboplatin+paclitaxel, and other combinations were tested or are being tested in clinical trials.

In certain embodiments, the ICI therapy is used in combination with targeted cancer therapy, sometimes called "molecularly targeted therapy". In certain embodiments, the targeted therapy drugs are small molecules such as bortezormib (Velcade), sunitinib (Sutent). In certain embodiments, the targeted therapy drugs are monoclonal antibodies such as bevacizumab (Avastin), panitumumab (Vectibix), daratumumab (Darzalex). In certain embodiments, an anti-PD-1 is used in combination with sunitinib (Sutent) or pazopanib (Votrient) that was tested for treatment of RCC, or a combination of anti-CTLA-4 ipilimumab with BRAF inhibitor dabrafenib (Tafinlar).

In certain embodiments, the ICI therapy is used in combination with anti-angiogenic therapy, for example, with a mAb that targets VEGF. Thus, the combination may be of Ipilimumab and bevacizumab.

In certain embodiments, the ICI therapy is used in combination with other immunotherapies such as cancer vaccines, immunomodulators, immunostimulatory cytokines, e.g., GM-CSF, IFN-α, TGF-β, IL-10, IL-18, and IL-21, or oncolytic viruses. In certain embodiments, anti-CTLA-4 ipilimumab or anti-PD-1 pembrolizumab is used in combination with oncolytic virus talimogene laherparepvec (T-VEC).

In accordance with the invention, the cancer therapy is related to all types of cancer, primary or metastatic, in all stages of the disease. The cancer may be selected from sarcomas, carcinomas, myelomas, lymphomas and leukemias. In certain embodiments, the cancer is of the sarcoma type, e.g. soft tissue sarcoma, osteosarcoma, in certain embodiments, the cancer is a carcinoma including, but without being limited to, melanoma, brain, head, neck, bone, nasopharyngeal, liver, gastrointestinal, biliary, bile duct, esophageal, colon, rectal, colorectal, ovarian, breast, cervical, prostate, renal, penile, testicular, skin, lung, chest, pancreatic, thymus, thyroid, or bladder cancer.

In certain embodiments, the cancer is a lymphoma, a cancer of the lymphatic system that may be a Hodgkin lymphoma or a non-Hodgkin lymphoma. The non-Hodgkin lymphoma may be B-cell lymphoma or T-cell lymphoma.

In certain embodiments, the cancer is leukemia, a cancer of the body's blood-forming tissues, including the bone marrow and the lymphatic system. In certain embodiments, the leukemia is selected from acute lymphocytic leukemia (ALL), acute myeloid leukemia (AML), chronic lymphocytic leukemia (CLL) or chronic myeloid leukemia (CML). In certain embodiments, the cancer is multiple myeloma.

In certain embodiments, the cancer is non-small cell lung cancer (NSCLC). In certain embodiments, the cancer is advanced (stage III or IV) or metastatic NSCLC.

In certain embodiments, the cancer is metastatic melanoma, renal-cell carcinoma (RCC), classic Hodgkin's lymphoma (HL), bladder carcinoma, Merkel cell carcinoma, head and neck cancer, or solid tumors with mismatch repair-deficiency The host-driven factors/biomarkers identified by the method of the invention after administration of an immune checkpoint inhibitor to a cancer patient are specific to: (i) the cancer patient; and (ii) the immune checkpoint inhibitor. This is the "host response" that provides specific information about the cancer patient and allows the prediction in a personalized form to help diagnose, plan treatment, find out how well treatment is working, or make a prognosis If the treatment is with one single ICI, the factors generated by the host/patient are specific to this particular ICI. If the treatment is carried out with a combination of two ICIs, the factors generated by the host/patient are specific to this combination of ICIs. If treatment is with the ICI in combination with another cancer therapy, the factors generated by the host/patient are specific to this combination.

In certain embodiments, the biomarkers are molecular factors such as cytokines, chemokines, growth factors, enzymes or soluble receptors. Some of these factors induce cells that affect the tumor and contribute to tumor angiogenesis and cancer re-growth, thereby promoting resistance to the therapy used. Examples of such cells include bone-marrow derived cells (BMDCs) that are mobilized from the bone-marrow compartment by cytokines and growth factors such as G-CSF and SDF-1α, and subsequently colonize the treated tumors and promote cancer therapy resistance, particularly, but not exclusively, chemotherapy resistance. Other cells are immune cells such as macrophages and antigen-presenting cells, or stromal cells within the tumor microenvironment which play a pivotal role in tumor progression.

The host-mediated cellular and molecular mechanisms that contribute to tumor resistance to a cancer therapy are based on the biological functions of the factors and/or cells generated in the host by the particular cancer therapy. Each factor may exhibit one or more biological functions or activities.

In certain embodiments, the factors are tumorigenic and contribute to tumor growth. In certain embodiments, the tumorigenic factors are pro-angiogenic. In other embodiments, the tumorigenic factors are pro-inflammatory/chemotactic. In yet other embodiments, the tumorigenic factors are proliferative growth factors.

In certain embodiments, the pro-angiogenic factors include, without being limited to, ANG (angiogenin); angiopoietin-1; angiopoietin-2; bNGF (basic nerve growth factor); cathepsin S; Galectin-7; GCP-2 (granulocyte chemotactic protein, CXCL6); G-CSF (granulocyte-colony stimulating factor); GM-CSF (granulocyte-macrophage colony stimulating factor, also known as colony-stimulating factor 2, CSF2); PAI-1 (plasminogen activator Inhibitor-1); PDGF (platelet-derived growth factor) selected from PDGF-AA, PDGF-BB, PDGF-AB; PlGF (or PLGF, placental growth factor); PlGF-2; SCF (stem-cell factor); SDF-1 (CXCL12, stromal cell-derived factor-1); Tie2 (or TIE-2, an endothelial receptor tyrosine kinase); VEGF (vascular endothelial growth factor) selected from VEGF-A, VEGF-C and VEGF-D; VEGF-R1; VEGF-R2; VEGF-R3.

In certain embodiments, the pro-inflammatory and/or chemotactic factors include, without being limited to, 6Ckine (CCL21, Exodus-2); angiopoietin-1; angiopoietin-2; BLC (CXCL13, B lymphocyte chemoattractant or B cell-attracting chemokine 1 (BCA-1); BRAK (CXCL14); CD186 (CXCR6); ENA-78 (CXCL5, Epithelial cell derived neutrophil activating peptide 78); Eotaxin-1 (CCL11); Eotaxin-2 (CCL24); Eotaxin-3 (CCL26); EpCAM (Epithelial cell adhesion molecule); GDF-15 (growth differentiation factor 15, also known as macrophage inhibitory cytokine-1, MIC-1); GM-CSF; GRO (growth-regulated oncogene); HCC-4 (CCL16, human CC chemokine 4); I-309 (CCL1); IFN-γ; IL-1α; IL-1β; IL-1R4 (ST2); IL-2; IL-2R; IL-3; IL-3Rα; IL-5; IL-6; IL-6R; IL-7; IL-8; IL-8 RB (CXCR2, interleukin 8 receptor, beta); IL-11; IL-12; IL-12p40; IL-12p70; IL-13; IL-13 R1; IL-13R2; IL-15; IL-15Ra; IL-16; IL-17; IL-17C; IL-17E; IL-17F; IL-17R; IL-18; IL-18BPa; IL-18 Rα; IL-20; IL-23; IL-27; IL-28; IL-31; IL-33; IP-10 (CXCL10, interferon gamma-inducible protein 10); I-TAC (CXCL11, Interferon-inducible T-cell alpha chemoattractant); LIF (Leukemia inhibitory factor); LIX (CXCL5, lypopolysaccharide-induced CXC chemokine); LRP6 (low-density lipoprotein (LDL) receptor-related protein-6); MadCAM-1 (mucosal addressin cell adhesion molecule 1); MCP-1 (CCL2, monocyte chemotactic protein 1); MCP-2 (CCL8); MCP-3 (CCL7); MCP-4 (CCL13); M-CSF (macrophage colony-stimulating factor, also known as colony stimulating factor 1 (CSF1); MIF (macrophage migration inhibitory factor); MIG (XCL9, Monokine induced by gamma interferon); MIP-1 gamma (CCL9, macrophage inflammatory protein-1 gamma); MIP-1a (CCL3); MIP-10; MIP-16 (CCL15); MIP- 3a (CCL20); MIP-30 (CCL19); MPIF-1 (CCL23, Myeloid progenitor inhibitory factor 1); PARC (CCL18, pulmonary and activation-regulated chemokine); PF4 (CXCL4, platelet factor 4); RANTES (CCL5, regulated on activation, normal T cell expressed and secreted); Resistin; SCF; SCYB16 (CXCL16, small inducible cytokine B16); TACI (transmembrane activator and CAML interactor); TARC (CCL17, CC thymus and activation related chemokine); TSLP (Thymic stromal lymphopoietin; TNF-α (tumor necrosis factor-α); TNF R1; TRAIL-R4 (TNF-Related Apoptosis-Inducing Ligand Receptor 4); TREM-1 (Triggering Receptor Expressed On Myeloid Cells 1).

In certain embodiments, the proliferative factors include, without being limited to, Activin A; Amphiregulin; Axl (AXL, a receptor tyrosine kinase); BDNF (Brain-derived neurotrophic factor); BMP4 (bone morphogenetic protein 4); cathepsin S; EGF (epidermal growth factor); FGF-1 (fibroblast growth factor 1); FGF-2 (also known as bFGF, basic FGF); FGF-7; FGF-21; Follistatin (FST); Galectin-7; Gas6 (growth arrest-specific gene 6); GDF-15; HB-EGF (heparin-binding EGF); HGF; IGFBP-1 (Insulin-like growth factor binding protein-1); IGFBP-3; LAP (Latency-associated peptide); NGF R (nerve growth factor receptor); NrCAM (neuronal cell adhesion molecule); NT-3 (neurotrophin-3); NT-4; PAI-1; TGF-α (transforming growth factor-α); TGF-β; and TGF-β3; TRAIL-R4 (TNF-Related Apoptosis-Inducing Ligand Receptor 4).

In certain embodiments, the pro-metastatic factors include, without being limited to, ADAMTS1 (A disintegrin and metalloproteinase with thrombospondin motifs 1); cathepsin S; FGF-2; Follistatin (FST); Galectin-7; GCP-2; GDF-15; IGFBP-6; LIF; MMP-9 (Matrix metallopeptidase 9, also known as 92 kDa gelatinase or gelatinase B (GELB); pro-MMP9; RANTES (CCL5); SDF-1 (stromal cell-derived factor-1, also known as CXCL12) and its receptor CXCR4.

The factors may also be anti-tumorigenic factors, e.g., anti-angiogenic, anti-inflammatory and/or anti-proliferative growth factors.

In certain embodiments, the circulating factors indicating a host response to ICI include, but are not limited to, ADAMTS1, amphiregulin; Axl; CCL5/RANTES; CCL17/TARC; EGF; Eotaxin-2; FGF-21; Gas6; G-CSF; GM-CSF; HGF; IFN-gamma; IL-1Ralpha; IL-2; IL-6; IL-7; IL-10; IL-12p40; IL-13; IL-33; I-TAC; MadCAM-1; MCP-5; TACI; M-CSF; MMP-9; PDGF-BB; pro-MMP9; SCF.

In accordance with the present invention, many of the factors that were upregulated in response to anti-PD-1 treatment are key players in pro-tumorigenic and pro-metastatic processes such as angiogenesis, inflammation, chemotaxis and proliferation. Upregulated pro-angiogenic factors include: G-CSF; GM-CSF; and PDGF-BB. Up-regulated pro-inflammatory and/or chemotactic factors include: CCL17/TARC; CCL5/RANTES; G-CSF; GM-CSF; IFN-gamma; IL-1Ralpha; IL-2; IL-6; IL-7; IL-10; IL-12p40; IL-13; IL-33; and M-CSF. Upregulated proliferative growth factors include: FGF-21; Gas6; and HGF. Upregulated pro-metastatic factors include: MMP-9.

In accordance with the present invention, many of the factors that were upregulated in response to anti-PD-L1 treatment are key players in pro-tumorigenic and pro-metastatic processes such as inflammation, chemotaxis and proliferation. Upregulated pro-angiogenic factors include: G-CSF; and SCF. Upregulated pro-inflammatory and/or chemotactic factors include: Eotaxin-2; G-CSF; IL-1ra; IL-6; IL-7; IL-33; I-TAC; MadCAM-1; MCP-5; SCF; and TACI. Upregulated proliferative growth factors include: amphiregulin; Axl; EGF; and HGF. Upregulated pro-metastatic factors include: ADAMTS1 and pro-MMP9.

In another aspect, the present invention provides a kit comprising a plurality of antibodies, each antibody of the plurality of antibodies selectively binding to each of a plurality of factors that promote responsiveness or non-responsiveness of a cancer patient to treatment with an immune checkpoint inhibitor, and instructions for use.

In certain embodiments, the kit is any type of antibody array to detect the levels of proteins. In certain embodiments, the kit is a sandwich or enzyme-linked immunosorbent assay (ELISA) that uses solid-phase enzyme immunoassay (EIA) to detect the presence of a substance, usually an antigen, in a liquid sample or wet sample. According to the present invention, this liquid sample is a biological sample obtained from a cancer patient undergoing treatment with an ICI.

In certain embodiments, the kit comprises a plurality of human monoclonal antibodies, each binding specifically to a pro-tumorigenic factor having pro-angiogenic, pro-inflammatory/chemotactic, proliferative and/or pro-metastatic activity, at least some of these pro-tumorigenic factors being factors that have been previously identified according to the present invention to be predictive of a favorable or a non-favorable response of a cancer patient to treatment with an immune checkpoint inhibitor. The kit will of course comprise additional antibodies for binding to potential candidates pro-tumorigenic factors. The numbers of monoclonal antibodies in the kit will be determined according to the producer's decision.

Thus, in certain embodiments, the kit of the invention comprises an array of monoclonal antibodies, at least 30 of said monoclonal antibodies each specifically binds to a factor selected from the following 30 factors: ADAMTS1, amphiregulin; Axl; CCL5/RANTES; CCL17/TARC; EGF; Eotaxin-2; FGF-21; Gas6; G-CSF; GM-CSF; HGF; IFN-gamma; IL-1Ralpha; IL-2; IL-6; IL-7; IL-10; IL-12p40; IL-13; IL-33; I-TAC; MadCAM-1; MCP-5; TACI; M-CSF; MMP-9; PDGF-BB; pro-MMP9; and SCF.

In certain preferred embodiments, the kit is for use according to the present invention.

In another aspect, the present invention provides a method for treating a cancer patient with an immune checkpoint inhibitor (ICI).

In one embodiment, there is provided a method of treating a cancer patient with an immune checkpoint inhibitor (ICI), the method comprising the steps of:
(i) performing an assay on a biological sample obtained from the cancer patient after a session of treatment with the ICI to determine the levels of one or more factors induced in the circulation of said cancer patient by the ICI;
(ii) establishing the fold change for each of the one or more factors of (i) by comparing the level of each of the one or more factors of (i) with a reference level for each of the one or more factors of (i) in a biological sample obtained from the cancer patient before said session of treatment with the ICI; and
(iiia) if the cancer patient has a non-favorable response to the treatment with said ICI based on the fold change of the level of the one or more factors established in (ii), then select a dominant factor among the one or more factors established in (ii) and treat the patient with the ICI in combination with an agent that blocks the dominant factor; or
(iiib) if the cancer patient has a favorable response to the treatment with said ICI based on the fold change of the level of the one or more factors established in (ii), then continue treating the patient with the ICI.

In another embodiment, there is provided a method of treating a cancer patient with an ICI, the method comprising the steps of:
(i) performing an assay on a biological sample selected from blood plasma, whole blood, blood serum or peripheral blood mononuclear cells obtained from the cancer patient at a time period after a session of treatment with said ICI, to determine the levels of one or more of a plurality of factors induced in the circulation of said cancer patient in response to treatment with said ICI, said one or more of the plurality of factors promoting responsiveness or non-responsiveness of the cancer patient to the treatment with said ICI;
(ii) obtaining reference levels for each of the one or more of the plurality of the induced factors of step (i) in a biological sample selected from blood plasma, whole blood, blood serum or peripheral blood mononuclear cells, obtained from the cancer patient before said session of treatment with the ICI;
(iii) establishing the fold change for each of the one or more of the plurality of the induced factors of step (i) by comparing the level of each induced factor of step (i) with the reference level of step (ii) for the same factor;
(iv) determining that the cancer patient has a favorable or a non-favorable response to the treatment with said ICI based on the fold change established in step (iii) for one or more of the plurality of induced factors of step (i); and
(iva) if the cancer patient has a non-favorable response to the treatment with said ICI based on the fold change established in (iii) for one or more of the plurality of the induced factors, then selecting a dominant factor among the one or more factors showing a fold change indicative of said non-favorable response, and treating the patient with the ICI in combination with an agent that blocks the dominant factor; or
(ivb) if the cancer patient has a favorable response to the treatment with said ICI based on the fold change of the level of the one or more factors established in (iii), then continuing the treatment of the cancer patient with the same ICI.

The biological samples of steps (i) and (ii) must be of the same type, and preferably they are both blood plasma.

According to the invention, when the session of treatment with the ICI is the first session of treatment with the ICI, the biological sample of step (i) is obtained from the cancer patient at about 20, 24, 30, 36, 40, 48, 50, 60, 72 hours or more, including up to one week or more or up to three weeks or more, after said first session of treatment, and the reference biological sample of step (ii) is obtained from the cancer patient at a time point including at about 72 hours or less, including at about 60, 50, 48, 40, 36, 30, 24, 20 hours or less or just before said first session of treatment with the ICI.

When the session of treatment with the ICI is one of multiple sessions of treatment that is not the first session of treatment with the ICI, the biological sample is obtained from the cancer patient at any time point between two consecutive sessions of treatment, wherein said biological sample is simultaneously the biological sample of step (i) and the reference biological sample according to step (ii) for the next session assay according to step (i). The time between two consecutive sessions of treatment may be of 2 or 3 weeks, depending on the ICI, and the biological sample may be obtained at day 1, 2, 3, 7, 14, or 21 days after the session of treatment that is not the first session of treatment with the ICI.

According to the invention, the fold-change established in step (iii) is defined by a fold change of ≥1.5 indicating upregulation or a fold change of ≤0.5 indicating down-regulation in the level of each of the one or more of the plurality of factors induced in the circulation of the cancer patient in response to the treatment with the ICI, these values being considered significant and predictive of a non-favorable or a favorable response of the cancer patient to the treatment with said ICI.

In accordance with the invention, the prediction of a favorable or a non-favorable response of the cancer patient to the treatment with the ICI is based on significant fold changes of one or more, optionally two or more, three or more, four or more, five or more, six or more, seven or more, eight or more, nine or more, ten or more, eleven or more, twelve or more, thirteen or more, fourteen or more, fifteen or more, twenty or more, or twenty-five or more, of the induced factors. These factors induced in the circulation of the cancer patient in response to treatment with the ICI are molecular factors including cytokines, chemokines, growth factors, enzymes and soluble receptors. These factors may be pro-tumorigenic or pro-metastatic factors, and the pro-tumorigenic factors may be pro-angiogenic, pro-inflammatory/chemotactic or proliferative growth factors.

In certain embodiments, there is an increase (up-regulation) of at least about 1.5-fold in the level of one or more of the pro-tumorigenic or pro-metastatic factors, and the prediction is of a non-favorable response of the cancer patient to the treatment with the ICI. In certain embodiments, there is a decrease (down-regulation) of at least about 0.5-fold in the level of one or more of the pro-tumorigenic or pro-metastatic factors, and the prediction is of a favorable response of the cancer patient to the treatment with the ICI.

According to the method of the invention for treating a cancer patient with an ICI, if the cancer patient has a non-favorable response to the treatment with said ICI based on the fold change established in (iii) for one or more of the plurality of the induced factors, a selection of a dominant factor is made among the one or more factors showing a fold change indicative of said non-favorable response, and the patient is treated with the same ICI in combination with an agent that blocks the dominant factor.

The terms "block", "neutralize" or "inhibit" are herein used interchangeably and refer to the capability of an agent of preventing the factor from exerting its function/biological activity.

As used herein, the term "dominant factor" denotes a potent factor that may be upstream of a signaling pathway that affects a biological process that is vital for the living cell and living organism. These biological processes include proliferation, inflammation, metastasis, and others, and are made of several signaling pathways ultimately leading to activation or inhibition of the biological process. A "signaling pathway" is a row of events in which proteins in the same pathway transfer signal to each other. After the first protein in a pathway receives a signal, it activates another protein which activates another protein and so forth, ultimately leading to activation of one or more cell functions.

A "dominant factor" may also be a key factor that highly interacts with, and highly affects, many other factors/proteins. According to the invention, the dominant factors are selected based on an algorithm which identifies the protein-protein interactions of factors based on the literature. When a factor has more interactions, it serves as a hub and therefore it is a dominant factor. The term "protein-protein interactions" refers to physical interactions or cross-talk between two or more proteins, resulting in activation or inhibition of signal transduction or protein activity. The term "protein hubs" refers to highly connected proteins that play central and essential role in biological processes and thus may confer the host with resistance, limit or counteract the effectiveness of the treatment of the cancer patient with the cancer therapy modality.

Examples of dominant factors include, without limitation, Amphiregulin, EGF, EGFR, FGF, IFN-γ, IL-1β, IL-2, IL-6, MMP-9, PDGF, TNF-α and VEGF-A.

To illustrate their qualifications as dominant factors, the properties of some of these factors is provided herein. Interleukin-1β(IL-1β, IL-1b) is a cytokine member of the IL-1 family, produced by different immune cells including macrophages. It is a potent mediator of the inflammatory response and also known to be involved in several biological processes such as cell proliferation and apoptosis, as well as cell differentiation. IL-1b was mostly investigated as a protein that initiates the pro-inflammatory cascade. It physically interacts with enzymes such as CASP1, IL1RA, IL1R1, CMA1, IL1RB, IL1A, IL1R2; genetically interacts with MAPK8IP2, ZNF675 and UBEN2N; and is co-expressed with A2M, CXCL8, IL18, CAASp1, IL1R1 and others. Thus, IL-1b serves as a hub for interactions with a large number of proteins that affect several biological pathways including cell proliferation, apoptosis and differentiation as well as inflammation and angiogenesis.

Another dominant factor is Interleukin-6 (IL-6), which is a cytokine that acts mainly as a pro-inflammatory factor but also sometimes as an anti-inflammatory factor produced by muscle cells and as a result downregulate a number of pro-inflammatory proteins such as IL-1, IL-10 and TNF-α. IL-6 is involved in a number of biological processes including bone formation, disruption of blood brain barrier, macrophage activation and innate immune system contribution, stimulates the synthesis of neutrophils and B cells, and is also involved in neurological activities such as disorders, stress and depression. IL6 interacts and affects a large number of proteins: it physically interacts with HRH1, OSM, IL6ST, IL6R and ZBTB16, and was found to be co-expressed with a large number of proteins such as PTPRE, CSF3, CCL2, CXCL8, CXCL3, ICAM1 SELE, NFKBIZ among others. IL6 is involved in a number of pathways mediated by proteins such as LRPPRC, OSM, PTPRE, PIAS1 and IL6R. As such, IL6 serves as a dominant factor for a number of biological processes involved in immune cell activity, cell genesis, and cell-cell interactions.

A further dominant factor, vascular endothelial growth factor A (VEGF-A), is a growth factor that stimulates the formation of new blood vessels. It is involved in both angiogenesis (endothelial cell proliferation) as well as vasculogenesis (bone marrow-derived endothelial cell precursors and their differentiation). VEGF is important for embryonic cell development and neuronal development in the fetus, and is involved in leukocyte proliferation and differentiation, inflammation and several diseases such as age-related macular degeneration and the majority of cancers. VEGF-A physically interacts with a large number of proteins such as NRP1, NRP2, KDR, FLT1, PGF, THBS1, SPARC, GCP1 and VEGFC; it is co-expressed with SEMA3F, SHB, THBS1, FLT1 and VEGFC; it is involved with proteins of various pathways including PGF, CD2AP, IQGAP1, NEDD4; and it affects a number of biological processes such as angiogenesis, tumorigenesis, cell viability, proliferation and differentiation. As such, VEGF-A is considered a dominant factor, and vital factor for various biological processes both in normal physiological conditions as well as in disease states.

In certain embodiments, the selected dominant factor shows a fold change of ≥1.5 indicative of a non-favorable response of the cancer patient to the treatment with the ICI, and the treatment of the patient with said ICI may proceed in combination with an agent that blocks said dominant factor or the receptor thereof.

In certain embodiments, the dominant factor is selected from factors including amphiregulin, EGF, EGFR, FGF, IFN-γ, IL-1β, IL-2, IL-6, MMP9, PDGF, TNF-α and VEGF-A.

In certain embodiments, the dominant factor is MMP9, the ICI is an anti-PD-1 or anti-PD-L1 monoclonal antibody, and the cancer patient is treated with the ICI in combination with a MMP-9 inhibitor including SB-3CT.

In certain embodiments, the dominant factor is amphiregulin, the ICI is an anti-PD-1 or anti-PD-L1 monoclonal antibody, and the cancer patient is treated with the ICI in combination with an anti-amphiregulin antibody.

The invention will now be illustrated by the following non-limiting Examples.

EXAMPLES

Introduction

As discussed hereinbefore, recent clinical studies report that patients may sometimes develop resistance to ICIs, or may not respond to ICI therapy (Sharma et al., 2017). We describe herein that the cancer patient, i.e., the host, generates pro-tumorigenic factors in response to ICI therapy, which in turn contribute to tumor re-growth, progression and resistance to therapy. In order to identify the factors that contribute to this mechanism, we perform our in vivo experiments in both non-tumor- and tumor-bearing immunocompetent mice. This approach allows us to distinguish between the therapeutic anti-tumor activity of ICIs and the effect of these drugs on host cells. We focus on ICIs that are extensively used in the clinic, including anti-PD1, anti-PD-L1 and anti-CTL-4 monoclonal antibodies, and use murine tumor models that are known to be responsive or resistant to specific ICIs. For example, CT26 colon and EMT-6 breast carcinoma cell lines respond to anti-CTLA-4 and anti-PD-L1, respectively (Duraiswamy et al., 2013; Swart et a., 2013), whereas MC38 colon and 4T1 breast carcinoma cell lines are resistant or only modestly responsive to some ICIs (including anti-PD-1) (De Henau et al., 2016; Kodumudi et al., 2016), as also tested in our laboratory (not shown).

Materials and Methods

Materials

The following antibodies were purchased from BioXCell, West Lebanon, NH, USA: InVivoMAb anti-mouse-PD-1 (catalog #BEO146); InVivoPlus anti-mouse-PD-L1 (catalog #BEO101); and InVivoMAb Isotype control IgG2b antibody, (catalog #BE0090). SB-3CT (IUPAC name: 2-(((4-phenoxyphenyl) sulfonyl)methyl)thiirane) was purchased from MedKoo Biosciences Inc (catalog number 406563). Anti-amphiregulin (catalog #AF989) was purchased from R&D systems. A 10 mM stock solution of SB-3CT was prepared in 100% DMSO (Sigma). For the in vivo experiment, the stock solution was diluted to a final concentration of 1.25 mg/ml in 10% DMSO in normal saline.

(i) Tumor cell culture: Murine EMT6 breast carcinoma cells were purchased from the American Type Culture Collection (ATCC, USA). The cells were passaged in culture for no more than 4 months after being thawed from authentic stocks, and were regularly tested and found to be mycoplasma-free (EZ-PCR mycoplasma test kit, Biological Industries, Israel). Cells were cultured in Dulbecco's modified eagle medium (DMEM) supplemented with 10% fetal bovine serum (FBS), 1% L-glutamine, 1% sodium-pyruvate and 1% penicillin-streptomycin (Biological Industries, Israel). Cells were cultured at 37° C. in 5% $CO_2$.

(ii) Animal treatment protocols and tumor models: Naïve 8-10 week old female BALB/c, SCID or NOD-SCID mice (Harlan, Israel) were intraperitoneally injected with anti-PD-1 or irrelevant IgG rat-anti-mouse antibodies (BioXCell, West Lebanon, NH, USA). In other experiments, naïve 8-10 week old female and male BALB/c or C57bl/6 mice (Harlan, Israel) were intraperitoneally injected with anti-PD-L1 or irrelevant IgG rat-anti-mouse antibodies (BioXCell, West Lebanon, NH, USA). In all cases, antibodies were administered at a dose of 200 µg/20 gr mouse, every other day over the period of 1 week (3 injections in total). EMT6 murine breast carcinoma cells ($5\times10^5$) were implanted into the mammary fat pad of 8-10 week old BALB/c mice. Tumor size was assessed regularly with Vernier calipers using the formula $width^2 \times length \times 0.5$. In some experiments, mice were injected through the tail vein with EMT6 cells ($25\times10^3$) to form experimental lung metastasis. Mouse survival was monitored daily, and when mice faced difficulty breathing or lost more than 15% of their body weight, they were euthanized. Mice were sacrificed at endpoint and tumors were processed as described below.

(iii) Plasma samples and conditioned medium preparation: Blood from control IgG-, anti-PD-1-, or anti-PD-L1-treated mice was collected into EDTA-coated tubes by cardiac puncture. Subsequently, plasma was isolated by centrifugation of whole blood at 1000 g, 4° C., for 20 minutes. Plasma was stored in aliquots at −80° C. until further use. Bone marrow derived cells were flushed from the femurs of IgG or anti-PD-1 treated mice. Bone marrow cells ($1\times10^6$ cells/ml) were cultured in serum-free DMEM for 24 hours to generate conditioned medium (CM).

(iv) Modified Boyden chamber assay: Serum-starved EMT6 cells ($0.2\times10^5$ cells) were cultured in the upper compartment of the Boyden chamber that was coated with either 50 µl Matrigel (BD Biosciences, Bedford, MA) for invasion assays or 100 µl fibronectin (10 µg/ml) for migration assays. The lower compartment was filled with DMEM medium containing 5% plasma obtained from IgG-treated or anti-PD-1 treated BALB/c, SCID or NOD-SCID mice. After 4 hours (for migration) or overnight (for invasion) incubation, the cells that migrated to the bottom filter, were fixed and stained with Crystal violet. Images were captured using a LEICA DMI 6000B fluorescence inverted microscope per ×100 objective-field (Leica Microsystems, Germany). At least 10 fields per group were evaluated. The percentage of positive pixels (representing cells) covering the bottom membrane compartment over the total pixels in the field was calculated using Photoshop SC2 V9.0 (San Jose, CA, USA). Experiments were carried out in triplicate, and were independently performed at least twice.

(v) Matrigel plug assay: Matrigel (0.5 ml, BD Biosciences, USA) was mixed with plasma obtained from IgG-treated or anti-PD-1-treated mice (at a ratio of 10:1, Matrigel:plasma, by volume). The Matrigel was injected subcutaneously into the flanks of BALB/c female mice, 7-8 weeks of age. Plugs were removed 10 days later, and were subsequently prepared as a single cell suspension for flow cytometric analysis or processed for histological analysis as described below.

(vi) Flow cytometry analysis: Matrigel plugs, tumors or spleens were harvested from mice and prepared as single cell suspensions. Bone marrow derived cells (BMDCs) were flushed from femurs. Blood was drawn by retro-orbital sinus bleed. In all cases, cells were immunostained with antibody mixtures to identify different cell types according to the following markers: Myeloid derived suppressor cells (MDSCs), CD11b+/Gr-1+/Ly6G+/Ly6C+; M1 macrophages, CD11c+/CD206−/F4/80+; M2 macrophages, CD11c−/CD206+/F4/80+; cytotoxic T lymphocytes (CTLs), CD8+/CD25+; T helper cells, CD4+; and T regulatory cells, CD4+/CD25+/FOXp3+. All monoclonal antibodies were purchased from Biolegend, BD Biosciences, or R&D systems and used in accordance with the manufacturers' instructions. At least 100,000 events were acquired using a Cyan ADP flow cytometer and analyzed with Summit v4.3 software (Beckman Coulter).

(vii) Immunohistochemistry: Matrigel plugs were stored in optimum cutting temperature (OCT) at −80° C., and cryosectioned (10 µm). Matrigel plug sections were stained with H&E (Emmonya Biotech Ltd, Bulgaria) to evaluate the colonization of host cells. Endothelial cells in Matrigel sections were detected by immunostaining using a CD31 antibody (1:100, BD Biosciences) and a Cy3-conjugated secondary antibody (1:200, Jackson ImmunoResearch). Images were captured using the Leica CTR 6000 system.

(viii) Antibody arrays: Three protein profiling experiments were performed. In the first experiment, plasma samples extracted from IgG- or anti-PD-1 treated female BALB/c mice were pooled per treatment group (n=5 per group). Samples were applied to a membrane-based Proteome Profiler Mouse XL Cytokine Array (R&D Systems; Cat no: ARY028) according to the manufacturer's instruction to screen a total of 111 factors. In the second experiment, plasma samples extracted from IgG- or anti-PD-L1 treated female or male BALB/c or C57bl/6 mice were pooled per group (n=7 per group). Samples were applied to a glass slide-based Quantibody Mouse Cytokine Array (RayBiotech, Cat no: QAM-CAA-4000) according to the manufacturer's instruction to screen a total of 200 factors. In the third experiment, plasma samples extracted from IgG- or anti-PD-1 treated female BALB/c or SCID mice were pooled per group (n=7 per group). Samples were applied to a glass slide-based Quantibody Mouse Cytokine Array (RayBiotech, Cat no: QAM-CAA-4000) according to the manufacturer's instruction to screen a total of 200 factors. For the membrane-based array, pixel densities on developed X-ray films were analyzed using transmission mode densitometer and image analysis software. For the glass slide-based arrays, the fluorescent readout was detected by a laser fluorescent scanner. In all cases, data was normalized and the fold changes for each factor on the arrays were determined by calculating the ratio of treated:control values.

(ix) Statistical analysis: Data are expressed as mean±standard deviation (SD). The statistical significance of differences was assessed by one-way ANOVA, followed by Tukey ad hoc statistical test using GraphPad Prism 5 software (La Jolla, CA). Student t-test was used in some experiments when comparing only two groups. Differences between all groups were compared with each other. For tumor growth experiments, statistical significance is assessed by multiple t-test. For survival analysis, differences are assessed by Log-rank Mantle-Cox. Differences were considered significant at p values below 0.05.

Figure 1B:
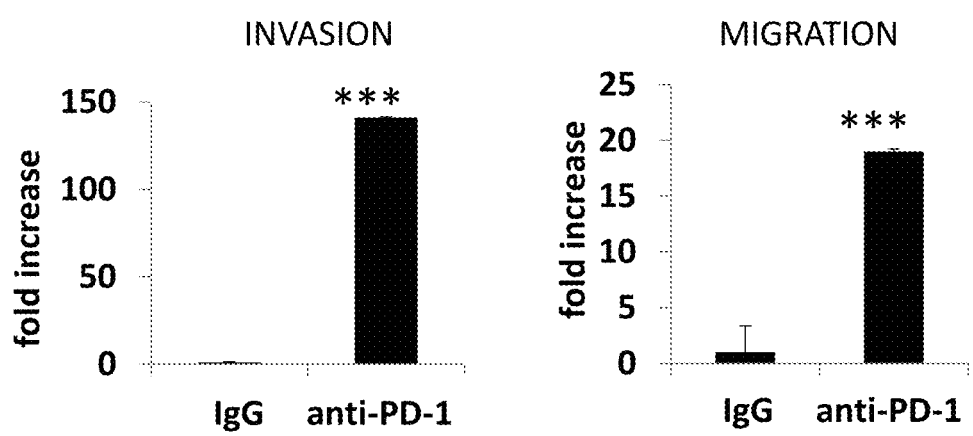
Figure 1C:
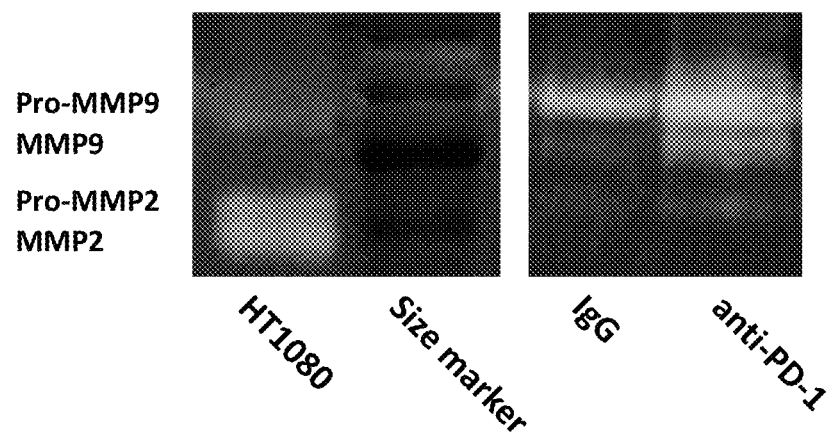
Figure 1D:
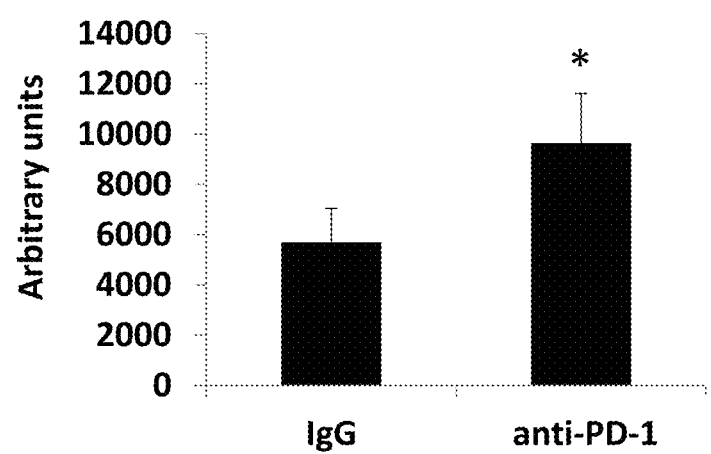

Example 1. In Vitro Assessment of Tumor Cell Aggressiveness in Response to Anti-PD-1 Treatment To test whether anti-PD-1 treatment induces a response in the host which in turn has a direct effect on tumor cell aggressiveness, in vitro migration and invasion assays were performed in the presence of plasma extracted from healthy naïve mice treated with anti-PD-1 or IgG control antibodies. The use of naïve mice allowed us to evaluate host-mediated effects, independent of tumor presence. To this end, non-tumor bearing Balb/c mice were intraperitoneally injected with anti-PD-1 or IgG control antibodies over a period of 1 week (3 injections in total). Mice were sacrificed, blood was drawn, and plasma was purified. The effect of the plasma samples on invasive and migratory properties of EMT6 tumor cells was assessed in vitro using a modified Boyden chamber assay. FIGS. 1A-B demonstrate that plasma from anti-PD-1-treated mice significantly enhances the invasive and migratory properties of EMT6 cells in comparison to plasma from IgG-treated control mice. These findings suggest that host-derived factors in the plasma of anti-PD-1-treated mice potentiate tumor cell aggressiveness. Since metalloproteinases (MMPs) are known to support tumor cell invasion and migration, we next evaluated the expression level of MMPs in conditioned medium (CM) of bone marrow derived cells (BMDCs) obtained from mice treated with anti-PD-1 or IgG control antibodies. We found that MMP9 was highly elevated in the CM of BMDCs obtained from mice treated with anti-PD-1 antibodies compared to control (FIGS. 1C-D). Collectively, these results suggest that, in response to anti-PD-1 treatment, host cells secrete factors into the circulation which support tumor cell aggressiveness.

Figure 2A:
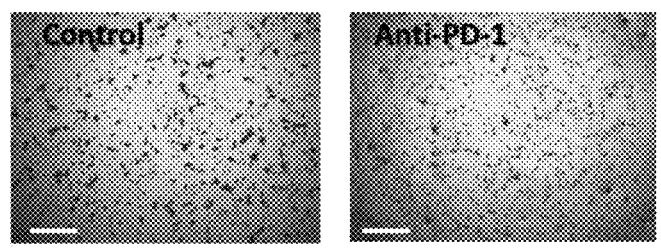
FIG. 2 A-B shows the effect of plasma derived from anti-PD-1-treated naïve SCID mice on the metastatic properties of tumor cells in vitro. Naïve (non-tumor bearing) 8-10 week old SCID mice were treated with anti-PD-1 or control antibodies for 1 week (n=3 mice/group). (A) Invasive properties of EMT6 cells were assessed in a Boyden chamber assay in the presence of plasma extracted from control and anti-PD-1-treated mice. Representative images of invading cells are shown. (B) Percentage of cell coverage was quantified from the images. Averages of 3 biological repeats are shown. ***$p<0.001$, using Student t-test.
Figure 2B:
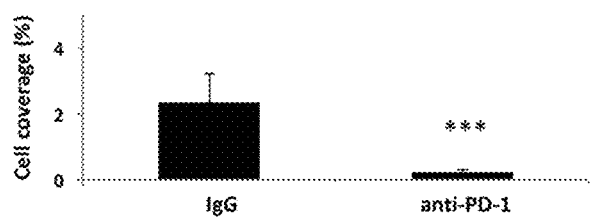
Figure 3A:
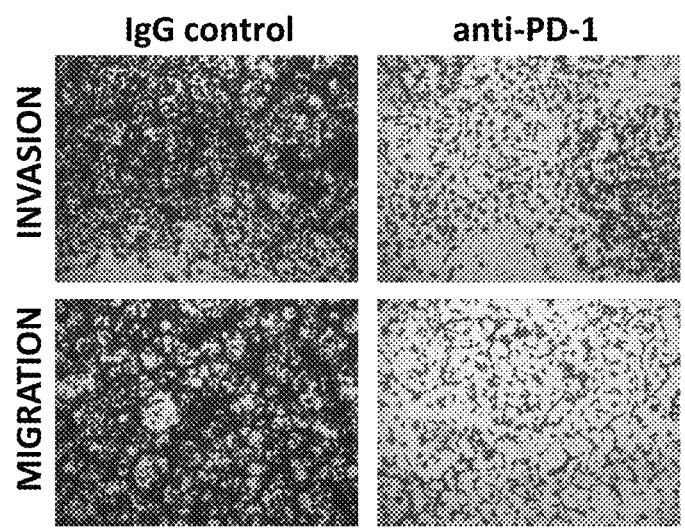
FIG. 3A-D shows the effect of plasma and bone marrow cells derived from anti-PD-1-treated naïve NOD-SCID mice on the metastatic properties of tumor cells. Naïve (non-tumor bearing) 8-10 week old NOD-SCID mice were treated with anti-PD-1 or control antibodies for 1 week (n=3 mice/group). (A) Invasion and migration properties of EMT6 cells were assessed in a Boyden chamber assay in the presence of plasma extracted from control and anti-PD-1-treated mice. Representative images of invading and migrating cells are shown. (B) Percentage of cell coverage was quantified from the images. Averages of 3 biological repeats are shown. (C-D) Bone marrow cells flushed from femurs of control or anti-PD-1-treated mice were cultured in serum-free DMEM for 24 hours ($1 \times 10^6$ cells/ml). Conditioned medium was collected and assessed by zymography to evaluate MMP activity. A representative zymography blot is shown in (C) and quantification of MMP9 is shown in (D). The experiment was performed in three biological repeats. ***$p<0.001$, using Student t-test.
Figure 3B:
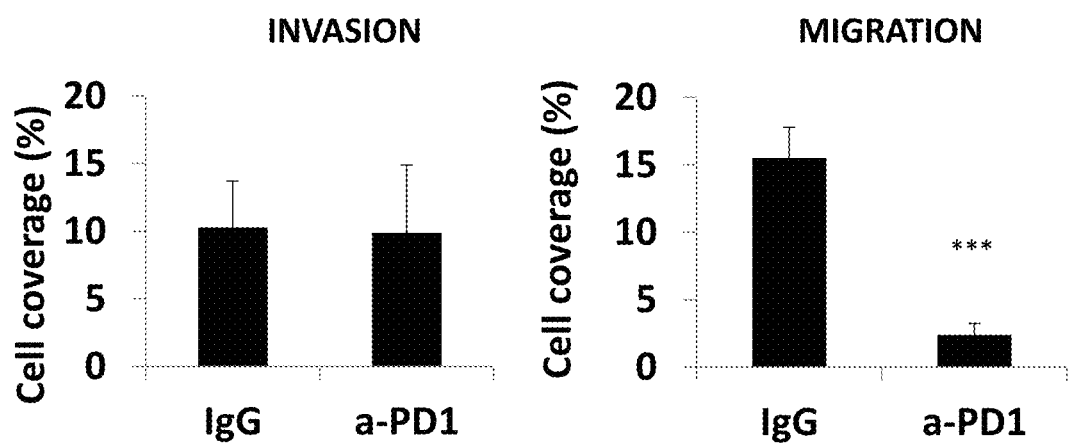
Figure 3C:
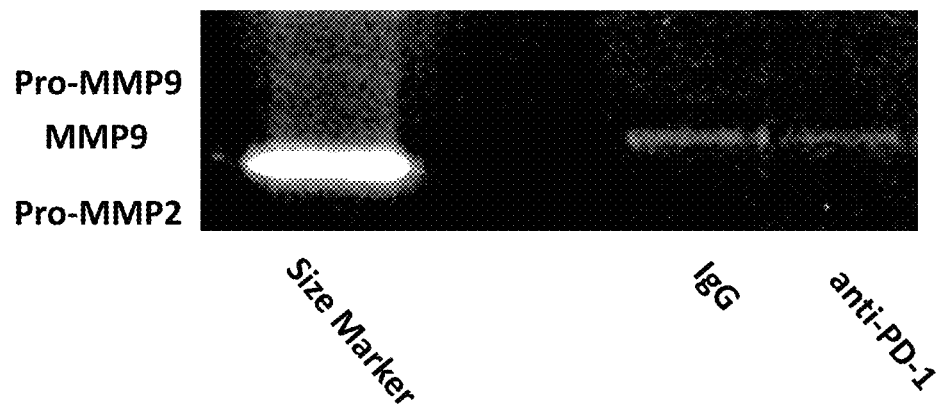
Figure 3D:
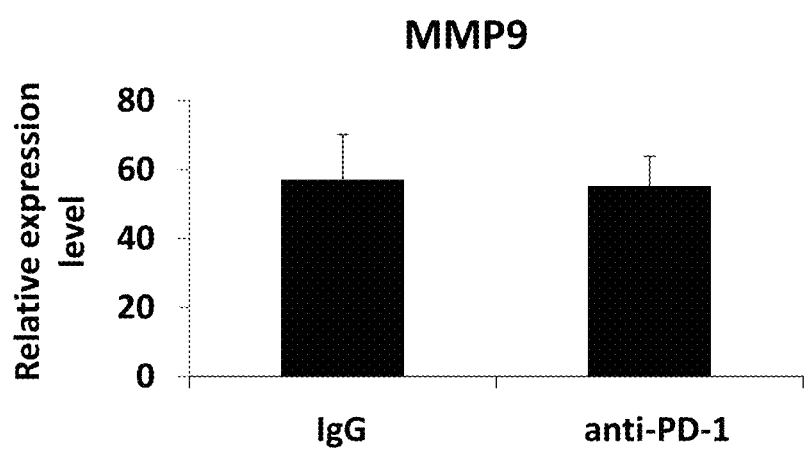

Example 2. Cells of the Adaptive Immune System Secrete Tumor-Supporting Factors in Response to Anti-PD-1 Treatment To identify the host cell types that secrete tumor-supporting factors in response to anti-PD-1 treatment, similar experiments to those described in Example 1 were performed. However, in this case, SCID CB17 mice, which lack adaptive immune cells, and NOD-SCID mice, which are deficient in adaptive immune cell types and dysfunctional in innate immune cell types, were used. Non-tumor bearing SCID or NOD-SCID mice were intraperitoneally injected with anti-PD-1 or IgG control antibodies over a period of 1 week (3 injections in total). Mice were sacrificed, blood was drawn, and plasma was purified. The effect of the plasma samples on invasive and migratory properties of EMT6 tumor cells was assessed in vitro using a modified Boyden chamber assay. Our results demonstrate that plasma from anti-PD-1-treated SCID mice inhibited the invasive properties of EMT6 cells, whereas plasma from NOD-SCID mice had no effect on invasion and inhibited migration of EMT6 cells in comparison to controls (FIG. 2, FIGS. 3A-B). We next evaluated the expression level of MMP9 in conditioned medium (CM) of bone marrow derived cells (BMDCs) obtained from NOD-SCID mice treated with anti-PD-1 or IgG control antibodies. As shown in FIGS. 3C-D, the levels of MMP9 were similar in CM from bone marrow cells extracted from anti-PD-1-treated and control mice. These collective results are in clear contrast to those described in Example 1 and shown in FIG. 1. They suggest that factors promoting tumor cell invasion and migration are secreted primarily by cells of the adaptive immune system in response to anti-PD-1 treatment.

Figure 4A:
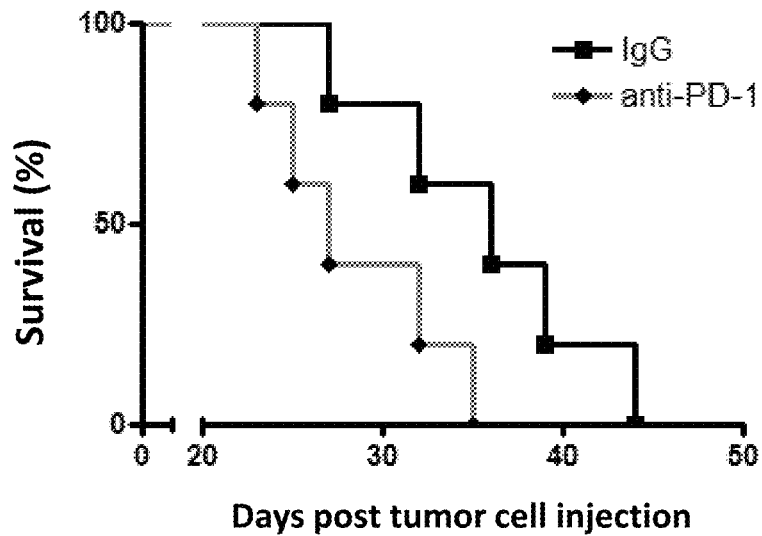
FIG. 4A-B shows that EMT6 cells pre-cultured with plasma from anti-PD-1-treated BALB/c mice increase mortality rate in an experimental lung metastasis assay. (A-B) EMT6 murine breast carcinoma cells were pre-cultured for 4 hours in the presence of plasma derived from control or anti-PD-1-treated BALB/c mice. The cells were washed and injected intravenously through the tail vein ($2.5 \times 10^4$ cells/mouse) to naïve 8 week old BALB/c mice to generate an experimental lung metastasis assay. Survival was assessed over time. Kaplan-Meier survival curves are shown for the first (A) and second (B) experiments in which n=5 and n=7-8 mice/group were used, respectively. $p<0.05$ in (A) and $p=0.055$ in (B).
Figure 4B:
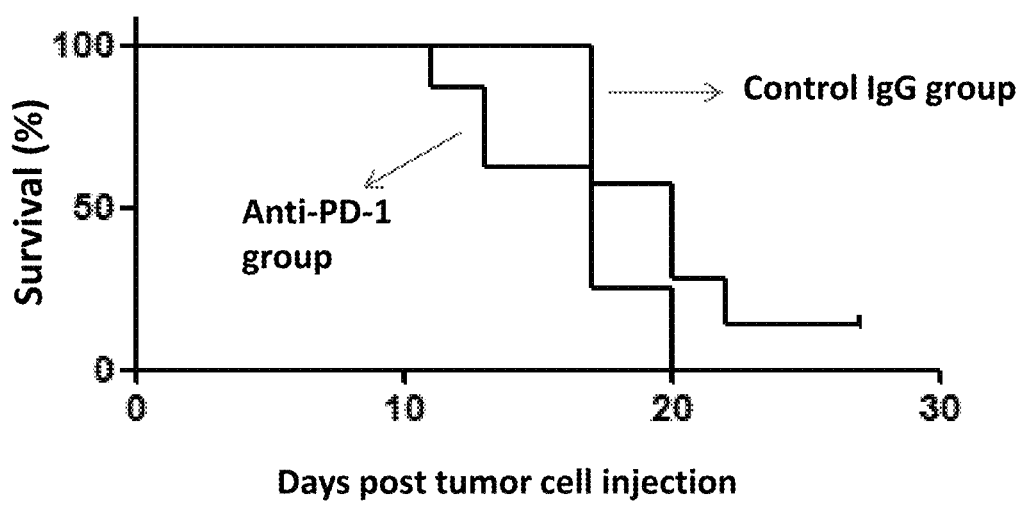

Example 3. In Vivo Assessment of Tumor Progression in Response to Anti-PD-1 Treatment To evaluate how the response of the host to anti-PD-1 treatment affects tumor fate, we studied the in vivo metastatic properties of tumor cells which had been pre-treated with plasma derived from anti-PD-1-treated naïve (non-tumor bearing) mice. To this end, EMT6 cells were pre-cultured for 4 hours in serum-free medium containing 10% plasma which was extracted from naïve BALB/c mice treated with anti-PD-1 antibodies or control IgG. The cells were washed and subsequently injected intravenously to the tail vein of naïve BALB/c mice to generate an experimental pulmonary metastasis model. The results in FIG. 4 demonstrate that mice injected with EMT6 cells which had been pre-exposed to plasma from anti-PD-1-treated mice exhibit an increased mortality rate in comparison to control mice injected with EMT6 cells pre-treated with plasma from IgG-treated mice. The lungs from all mice were removed and evaluated for metastasis. No significant differences were observed in the number of metastatic lesions in the lungs (data not shown).

Figure 5A:
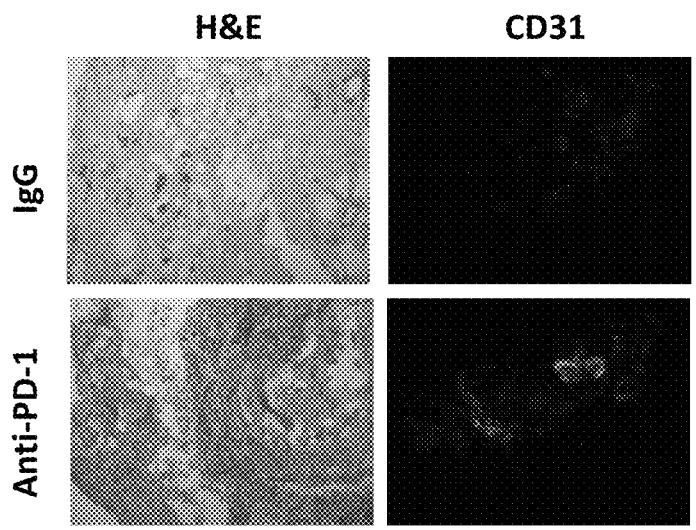
FIG. 5A-B shows the colonization of different host cell types in Matrigel containing plasma from anti-PD-1-treated mice. Plasma obtained from control or anti-PD-1-treated mice was mixed with Matrigel in a 1:10 ratio. Matrigel plugs were implanted into the flanks of naïve 8-10 week old BALB/c mice (n=4 mice/group). (A) After 10 days, the Matrigel plugs were removed, sectioned and subsequently stained with H&E (left micrographs) or CD31, an endothelial cell marker (in red, right micrographs). (B) In a parallel experiment, Matrigel plugs were prepared as single cell suspensions. Cell suspensions were evaluated for the indicated immune cell types using flow cytometry. $*p<0.05$; $p<0.01;*p<0.001$, as assessed by Student t-test.
Figure 5B:
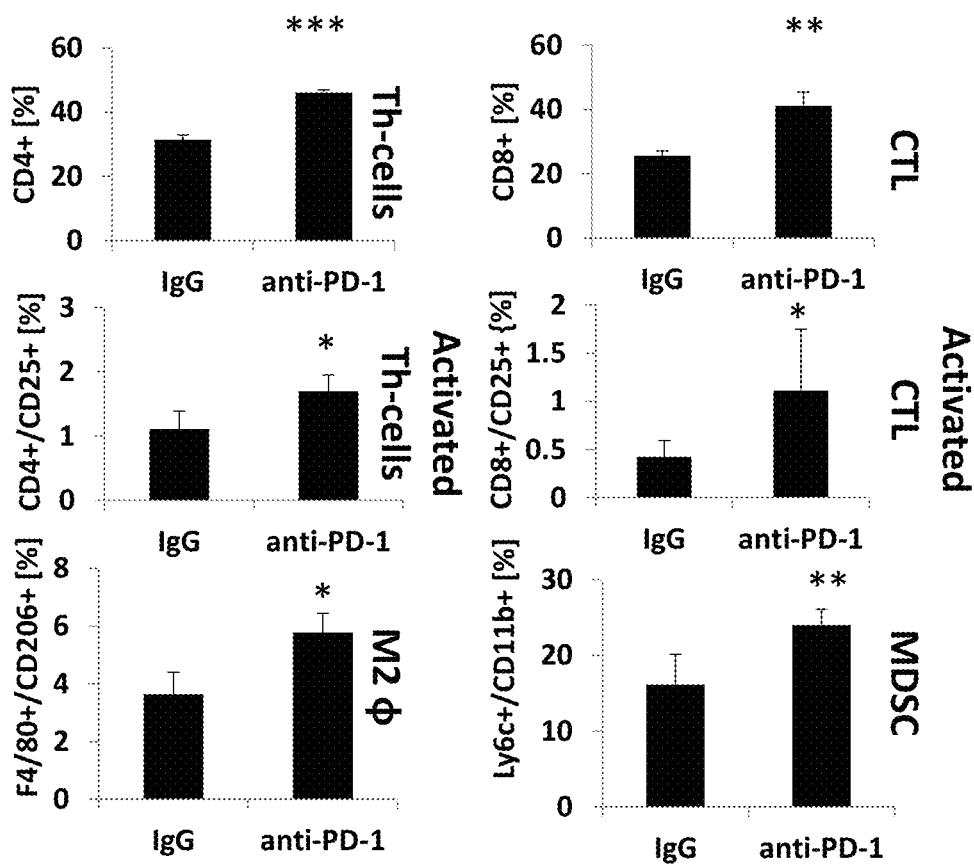

Example 4. Anti-PD-1 Treatment Promotes the Colonization of Tumor-Supporting Host Cells in Matrigel Plugs To characterize the effect of anti-PD-1 treatment on the host cell composition in the tumor microenvironment, a Matrigel plug assay was used. Matrigel is a material composed of tumor extracellular matrix found in the tumor microenvironment. The Matrigel was mixed in a 10:1 ratio with plasma from anti-PD-1-treated or IgG-treated mice. Subsequently, the Matrigel-plasma mixture was implanted into flanks of naïve BALB/c mice, and plugs were formed. After 10 days, plugs were removed, sectioned and immunostained for endothelial cells. As shown in FIG. 5A, blood vessels were more abundant in Matrigel plugs containing plasma from anti-PD-1-treated mice in comparison to the control. This suggests that host-derived, anti-PD-1-induced circulating factors promote angiogenesis. In a parallel experiment, Matrigel plugs were prepared as single cell suspensions and analyzed by flow cytometry to identify various immune cell types. As shown in FIG. 5B and Table 1, the levels of activated cytotoxic T lymphocytes (CTLs) and activated T helper cells were increased in Matrigel plugs containing plasma from anti-PD-1-treated mice in comparison to the control, in line with the therapeutic benefit of immunotherapy. However, the levels of other cell types associated with pro-tumorigenic activity including M2-like macrophages and MDSCs were also increased. These findings suggest that anti-PD-1 treatment induces a host response that involves tumor-supporting immune cells.

The results of the Matrigel assay prompted us to characterize the changes in immune cell composition in tumors and different organs in response to anti-PD-1 treatment. To this end, naïve non-tumor bearing BALB/c mice or BALB/c mice bearing EMT6 tumors (whose tumors had reached a size of 500 mm$^3$) were intraperitoneally injected with anti-PD-1 or IgG antibodies over the period of 1 week (3 injections in total). Mice were sacrificed and blood, spleens, BMDCs and tumors were extracted and analyzed by flow cytometry to identify different immune cell types. The data shown in Table 1 shows that within the tumor, as expected, CTLs were highly elevated and active, in line with the therapeutic benefit of immunotherapy. However, the levels of adaptive immune cells, including T helper and CTLs, were reduced in the blood and BMDCs of both non-tumor and tumor bearing anti-PD-1 treated mice in comparison to controls. In addition, in hematopoietic organs (e.g., spleen and BMDCs) of non-tumor or tumor bearing mice, the levels of innate immune cells, including M1 and M2 macrophages as well as MDSCs, fluctuated and sometimes increased. These results indicate that while in tumors, as expected, CTLs are active and promote anti-tumor activity, in other evaluated organs, tumor-supporting immune cells including M2 macrophages and MDSCs are elevated in response to anti-PD-1 treatment, and therefore may counteract the anti-tumor activity of CTLs.

Example 5. The Effect of Immune Checkpoint Inhibitor Therapy on Circulating Host-Derived Factors—a Protein Profiling Approach in Mice The data presented in FIGS. 1-5 suggest that anti-PD-1 therapy induces an upregulation of factors in the circulation which ultimately promotes tumor cell aggressiveness. Such effects may occur in response to other types of immune checkpoint inhibitor therapies. To identify host-derived circulating factors whose levels change in response to anti-PD-1 and anti-PD-L1 therapies, we performed 3 protein array-based screens using naïve (non-tumor bearing) mice. The use of naïve mice allows us to identify factors specifically generated by the host in response to therapy, independent of the tumor.

In the first screen, naïve 8-10 week old female BALB/c mice (n=3) were intraperitoneally injected with anti-PD-1 rat anti-mouse antibody (BioXCell, West Lebanon, NH, USA) at a dose of 200 μg/20 gr mouse every other day over a period of 1 week (3 injections in total). Control mice (n=3) were similarly injected with a rat-anti-mouse IgG antibody at the same dose. One week after the first injection, mice were sacrificed, and blood was collected into EDTA-coated tubes by cardiac puncture. Plasma was isolated by centrifugation of whole blood at 1300 g for 10 minutes at room temperature. Supernatants (representing the plasma samples) were collected and pooled per group. Aliquots were stored at −80° C. until further use. Plasma samples were applied to a membrane-based Proteome Profiler Mouse XL Cytokine Array (R&D Systems; Cat no: ARY028) to screen a total of 111 factors. A full list of cytokines, enzymes and growth factors detected by the array is shown in Table 2. Pixel densities on developed X-ray films were analyzed using transmission mode densitometer and image analysis software. Normalized data was analyzed to identify factors whose circulating levels were changed in response to anti-PD-1 treatment. Specifically, the fold change was determined for each factor by calculating the ratio of treatment:control values. Factors exhibiting a fold change of more than 1.5 or less than 0.5 were defined as being up- or down-regulated, respectively, in response to anti-PD-1 treatment. These factors and their respective fold changes are listed in Table 3. Many of the factors that were upregulated in response to anti-PD-1 treatment are key players in pro-tumorigenic and pro-metastatic processes such as angiogenesis, inflammation, chemotaxis and proliferation. Upregulated pro-angiogenic factors include: G-CSF; GM-CSF; and PDGF-BB. Up-regulated pro-inflammatory and/or chemotactic factors include: CCL17/TARC; CCL5/RANTES; G-CSF; GM-CSF; IFN-gamma; IL-1Ralpha; IL-2; IL-6; IL-7; IL-10; IL-12p40; IL-13; IL-33; and M-CSF. Upregulated proliferative growth factors include: FGF-21; Gas6; and HGF. Upregulated pro-metastatic factors include: MMP-9.

In the second screen, naïve 8-10 week old female BALB/c, male BALB/c, female C57Bl/6 or male C57Bl/6 mice (n=7 mice per group) were intra-peritoneally injected with anti-PD-L1 or control IgG antibodies (BioXCell, West Lebanon, NH, USA) every other day over a period of 1 week (3 injections in total) at a dose of 200 μg/20 gr mouse per injection. Twenty-four hours after the last administration, mice were sacrificed, blood was drawn and plasma was prepared. Plasma samples from each group were pooled and applied to a glass slide-based Quantibody Mouse Cytokine Array (RayBiotech, Cat no: QAM-CAA-4000) according to the manufacturer's instruction to screen a total of 200 factors. A full list of cytokines, enzymes and growth factors detected by the array is shown in Table 4. The fold changes were determined for each factor on the protein array by calculating the ratio of treated:control values. Factors exhibiting a fold change of more than 1.5 or less than 0.5 were defined as being up- or down-regulated, respectively, in response to anti-PD-L1 treatment. These factors, and their respective fold changes are listed in Table 5. The data demonstrate that the profiles of up- and down-regulated factors do not completely overlap when comparing between the different mouse strains or when comparing between males and females of the same strain. This suggests that the response to anti-PD-L1 treatment is genotype-dependent. This may reflect differences known to exist also among cancer patients, and therefore provides a rationale for testing the response of the host in patients in a personalized manner. Many of the factors that were upregulated in response to anti-PD-L1 treatment are key players in pro-tumorigenic and pro-metastatic processes such as inflammation, chemotaxis and proliferation. Upregulated pro-angiogenic factors include: G-CSF; and SCF. Upregulated pro-inflammatory and/or chemotactic factors include: Eotaxin-2; G-CSF; IL-1ra; IL-6; IL-7; IL-33; I-TAC; MadCAM-1; MCP-5; SCF; and TACI. Upregulated proliferative growth factors include: amphiregulin; Axl; EGF; and HGF. Upregulated pro-metastatic factors include: ADAMTS1 and pro-MMP9.

To gain insight into which host cell types secrete these pro-tumorigenic factors, we performed a similar screen, comparing between BALB/c and SCID mice treated with anti-PD-1 or control IgG antibodies. SCID mice carry the severe combined immune deficiency (SCID) mutation on the BALB/c background, and therefore lack functional adaptive immune cell types (B cells and T cells). Naïve 8-10 week old female BALB/c or SCID mice (n=7 mice per group) were intraperitoneally injected with anti-PD-1 or control IgG antibodies (BioXCell, West Lebanon, NH, USA) every other day over a period of 1 week (3 injections in total) at a dose of 200 μg/20 gr mouse per injection. Twenty-four hours after the last administration, mice were sacrificed, blood was drawn and plasma was prepared. Plasma samples from each group were pooled and applied to a glass slide-based Quantibody Mouse Cytokine Array (RayBiotech, Cat no: QAM-CAA-4000) according to the manufacturer's instruction to screen a total of 200 factors. A full list of cytokines, enzymes and growth factors detected by the array is shown in Table 4. The fold changes were determined for each factor on the protein array by calculating the ratio of treated:control values. Factors exhibiting a fold change of more than 1.5 or less than 0.5 were defined as being up- or down-regulated, respectively, in response to anti-PD-1 treatment. These factors, and their respective fold changes are listed in Table 6. Several factors were found to be up-regulated in response to anti-PD-1 treatment, some of which were specific to BALB/c and not SCID mice, e.g., ADAMTS1; amphiregulin, I-TAC and SCF. These results suggest that these specific factors are secreted by cells of the adaptive immune system in response to anti-PD-1 treatment.

Collectively, these results demonstrate that anti-PD-1 and anti-PD-L1 treatments induce a response in the host that supports tumor progression, counteracting the desired therapeutic effects of immune checkpoint inhibitor therapy.

Example 6. The Effect of Reducing Host-Derived MMP-9 Levels on ICI Therapy in a Primary Breast Tumor Model Matrix metallopeptidase 9 (MMP9) is an enzyme that belongs to the zinc-metalloproteinases family involved in the degradation of the extracellular matrix. MMP-9 was found to be induced in BALB/c mice following treatment with anti-PD-1 or anti-PD-L1, as shown in Examples 1 and 5 above, which demonstrate that: i) MMP-9 is secreted by bone marrow-derived cells of naïve BALB/c mice in response to anti-PD-1 treatment (FIG. 1C-D); ii) the plasma level of MMP9 is increased 5.4 fold in response to anti-PD-1 treatment in naïve BALB/c mice (Table 3); iii) the plasma level of pro-MMP-9 is increased 2-3 fold in response to anti-PD-L1 treatment in naïve BALB/c mice (Table 5).

To investigate whether inhibiting host-derived MMP9 improves the efficacy of anti-PD-1 or anti-PD-L1 therapy, the MMP2/MMP9 selective inhibitor SB-3CT is used in combination with anti-PD-1 or anti-PD-L1 antibodies. EMT6 murine breast carcinoma cells ($5 \times 10^5$) are orthotopically implanted in the mammary fat pad of female BALB/c mice, age 8-weeks, (Harlan, Israel). Tumor size is assessed regularly with Vernier calipers using the formula width$^2 \times$length$\times 0.5$. When tumors reach a size of 100 mm$^3$, mice are randomly assigned to the following treatment groups (n=6 mice per group): i) control; ii) anti-PD-1 monotherapy; iii) anti-PD-L1 monotherapy; iv) MMP2/MMP9 selective inhibitor SB-3CT monotherapy; v) anti-PD-1 and SB-3CT combination therapy; and vi) anti-PD-L1 and SB-3CT combination therapy. Anti-PD-1, anti-PD-L1 and IgG control antibodies are administered by intraperitoneal injections at a dose of 200 µg/20 g mouse every 3 days. SB-3CT is administered by intraperitoneal injections at a dose of 1 mg/20 g mouse every 3 days. Control mice are injected with IgG antibody and vehicle (10% DMSO in normal saline). Mice receiving either anti-PD-1 or anti-PD-L1 monotherapies are also injected with vehicle (10% DMSO in normal saline). Mice receiving SB3-CT monotherapy are also injected with IgG control antibodies. Tumor growth and mouse survival are monitored. At endpoint (when tumors reach a size of ~1500 mm$^3$), mice are sacrificed.

It is expected that treatment of BALB/c mice, which exhibit induced MMP9 in response to treatment with anti-PD1 or anti-PD-L1, with the combination of SB-3CT and either anti-PD-1 or anti-PD-L1 will be more effective in reducing tumor size and increasing survival than monotherapy with anti-PD-1 or anti-PD-L1 without the MMP9 inhibitor.

Example 7. The Effect of Reducing Host-Derived Amphiregulin Levels on ICI Therapy in a Primary Breast Tumor Model Amphiregulin is one of the ligands of the epidermal growth factor receptor (EGFR). Studies have demonstrated a functional role of amphiregulin in several aspects of tumorigenesis. Amphiregulin was chosen in light of our findings described in Example 5 above, which demonstrate that the plasma levels of amphiregulin are increased 2-3 fold in response to anti-PD-L1 treatment in naïve BALB/c and C57/bl/6 mice (Table 5), and 3.7 fold in response to anti-PD-1 treatment in BALB/c mice (Table 6).

To investigate whether inhibiting host-derived amphiregulin (which is upregulated in BALB/c mice in response to either anti-PD-1 or anti-PD-L1 treatment) improves the efficacy of anti-PD-1 or anti-PD-L1 therapy, the anti-mouse amphiregulin antibody AF989 is used in combination with anti-PD-1 or anti-PD-L1 antibodies. $5 \times 10^5$ EMT6 murine breast carcinoma cells are orthotopically implanted in the mammary fat pad of BALB/c mice. When tumors reach a size of 100 mm$^3$, mice are randomly assigned to the following treatment groups: i) control; ii) anti-PD-1 monotherapy; iii) anti-PD-L1 monotherapy; iv) monotherapy with anti-mouse amphiregulin antibody AF989; v) anti-PD-1 and AF989 combination therapy; and vi) anti-PD-L1 and AF989 combination therapy. Control mice are injected with IgG antibody. Anti-PD-1, anti-PD-L1 and IgG control antibodies are administered by intraperitoneal injections at a dose of 200 µg/20 g mouse every 3 days. Anti-amphiregulin antibody AF989 is administered by intraperitoneal injection at a dose of 10 µg/20 g mouse every 3 days. Tumor growth and mouse survival are monitored.

It is expected that treatment of BALB/c mice, which exhibit induced amphiregulin expression in response to treatment with anti-PD1 or anti-PD-L1, with a combination of AF989 antibody and either anti-PD-1 or anti-PD-L1 will be more effective in reducing tumor size and increasing survival than monotherapy with anti-PD-1 or anti-PD-L1 without the anti-amphiregulin antibody.

APPENDIX

TABLE 1

Changes in immune cell compositions from 3 experimental settings comparing anti-PD-1-treatment relative to control

| | Organ | Active Th | Active CTLs | B cells | T reg | NK cells | Active NK cells | Macrophages | MDSCs Gr1+/ CD11b+ |
|---|---|---|---|---|---|---|---|---|---|
| Naïve mice | Blood | ↓ | ↓ | ↓ | ↓ | ↑ | — | ↓ | — |
| | Spleen | — | ↓ | ↑ | ↓ | — | ↑ | M1↑ M2↓ | — |
| | BM | — | ↓ | ↑ | — | ↓ | ↓ | M1↑ M2↓ | ↓ |

TABLE 1-continued

Changes in immune cell compositions from 3 experimental settings comparing anti-PD-1-treatment relative to control

| | Organ | Active Th | Active CTLs | B cells | T reg | NK cells | Active NK cells | Macrophages | MDSCs Gr1+/CD11b+ |
|---|---|---|---|---|---|---|---|---|---|
| Tumor bearing mice | Tumor | ↑ | ↑* | — | ↓* | | | M1↑* M2↑ | Ly6C⁺/Ly6G⁻ ↓ Ly6C⁻/Ly6G⁺ ↓* |
| | Blood | — | — | ↓ | ↓* | — | — | — | Ly6C⁺/Ly6G⁻ ↓* Ly6C⁻/Ly6G⁺ ↓ |
| | Spleen | ↑ | ↑* | ↑ | ↑ | ↑ | ↑* | M1↓ M2↑ | Ly6C⁺/Ly6G⁻ ↓* Ly6C⁻/Ly6G⁺ ↑* |
| | BM | ↓* | ↓ | ↓ | — | ↓ | ↓ | M1↓ M2↑ | Ly6C⁺/Ly6G⁻ ↑ Ly6C⁻/Ly6G⁺ ↓ |
| Matrigel Plug assay | | ↑* | ↑* | — | ↑ | ↑ | ↑* | M1↑ M2↑ | Ly6C⁺/Ly6G⁻ ↑* Ly6C⁻/Ly6G⁺ ↑* |

*$p < 0.05$

TABLE 2

List of 111 factors participating in the antibody array screen performed with plasma from mice receiving immune-checkpoint inhibitor anti-PD-1 therapy
Proteome Profiler Mouse XL Cytokine Array (R&D Systems; Cat no: ARY028)

| | | | |
|---|---|---|---|
| Adiponectin/Acrp30 | CXCL9/MIG | IL-2 | PDGF-BB |
| Amphiregulin | CXCL10/IP-10 | IL-3 | Pentraxin 2/SAP |
| Angiopoietin-1 | CXCL11/I-TAC | IL-4 | Pentraxin 3/TSG-14 |
| Angiopoietin-2 | CXCL13/BLC/BCA-1 | IL-5 | Periostin/OSF-2 |
| Angiopoietin-like 3 | CXCL16 | IL-6 | Pref-1/DLK-1/FA1 |
| BAFF/BLyS/TNFS F13B | Cystatin C | IL-7 | Proliferin |
| C1q R1/CD93 | Dkk-1 | IL-10 | Proprotein Convertase 9/PCSK9 |
| CCL2/JE/MCP-1 | DPPIV/CD26 | IL-11 | RAGE |
| CCL3/CCL4 MIP-1 alpha/beta | EGF | IL-12p40 | RBP4 |
| CCL5/RANTES | Endoglin/CD105 | IE-13 | Reg3G |
| CCL6/C10 | Endostatin | IE-15 | Resistin |
| CCL11/Eotaxin | Fetuin A/AHSG | IL-17A | E-Selectin/CD62E |
| CCL12/MCP-5 | FGF acidic | IL-22 | P-Selectin/CD62P |
| CCL17/TARC | FGF-21 | IL-23 | Serpin E1/PAI-1 |
| CCL19/MIP-3 beta | Flt-3 Ligand | IL-27 | Serpin F1/PEDF |
| CCL20/MIP-3 alpha | Gas6 | IL-28 | Thrombopoietin |
| CCL21/6Ckine | G-CSF | IL-33 | TIM-1/KIM-1/HAVCR |
| CCL22/MDC | GDF-15 | LDL R | TNF-alpha |
| CD14 | GM-CSF | Leptin | VCAM-1/CD106 |
| CD40/TNFRSF5 | HGF | LIF | VEGF |
| CD160 | ICAM-1/CD54 | Lipocalin-2/NGAL | WISP-1/CCN4 |
| Chemerin | IFN-gamma | LIX | |
| Chitinase 3-like 1 | IGFBP-1 | M-CSF | |
| Coagulation Factor III/Tissue Factor | IGFBP-2 | MMP-2 | |
| Complement Component C5/C5a | IGFBP-3 | MMP-3 | |
| Complement Factor D | IGFBP-5 | MMP-9 | |
| C-Reactive Protein/CRP | IGFBP-6 | Myeloperoxidase | |
| CX3CL1/Fractalkine | IL-1 alpha/IL1F1 | Osteopontin (OPN) | |
| CXCL1/KC | IL-1 beta/IL-1F2 | Osteoprotegerin/TNFRSF11B | |
| CXCL2/MIP-2 | IL-1ra/IL-1F3 | PD-ECGF/Thymidine phosphorylase | |

TABLE 3

Summary of fold changes in the levels of circulating factors in anti-PD1-treated vs control BALB/c mice

| | Fold change (anti-PD-1 vs IgG) |
|---|---|
| C14 | 8.0 |
| CCL17/TARC | 5.0 |
| CCL19/MIP-3β | 1.5 |
| CCL21/6Ckine | 1.7 |
| CCL3/CCL4/MIP-1α/β | 1.8 |
| CCL5/RANTES | 13.0 |
| CD40/TNFRSF5 | 3.3 |
| Chemerin | 3.6 |
| Chitinase 3-like 1 | 2.6 |
| CXCL13/BCL/BCA-1 | 1.8 |
| CXCL9/MIG | 1.7 |
| Cystatin C | 21.2 |
| DKK-1 | 5.2 |
| Endoglin/CD105 | 2.8 |
| E-Selectin/CD62E | 1.6 |
| Fetuin A/AHSG | 14.6 |
| FGF acidic | 1.7 |
| FGF-21 | 2.5 |
| Gas 6 | 2.1 |
| G-CSF | 2.9 |
| GM-CSF | 2.2 |
| HGF | 3.9 |
| IFN-γ | 1.9 |
| IL-10 | 7.2 |
| IL-12 p40 | 23.5 |
| IL-13 | 2.5 |
| IL-1rα/IL-1F3 | 3.1 |
| IL-2 | 5.5 |
| IL-22 | 2.4 |
| IL-27 p28 | 2.3 |
| IL-28A/B | 2.0 |
| IL-33 | 3.0 |
| IL-4 | 1.5 |
| IL-6 | 15.6 |
| IL-7 | 5.2 |
| LDL R | 8.1 |
| Leptin | 2.0 |
| LIF | 1.8 |
| Lipocalin-2/NGAL | 4.8 |
| M-CSF | 6.9 |
| MMP-9 | 5.4 |
| Myeloperoxidase | 6.7 |
| Osteprotegerin/TNFRS11B | 1.8 |
| PDGF-BB | 4.1 |
| Pentraxin 2/SAP | 2.7 |
| Pentraxin 3/TSG-14 | 3.3 |
| Periostin/TSG-14 | 2.0 |
| Pref-1/DLK-1/FA1 | 5.8 |
| Proliferin | 5.8 |
| RBP4 | 4.5 |
| Serpin E1/PAI-1 | 3.8 |
| Serpin F1/PAI-1 | 1.6 |
| TIM-1/KIM-1/HAVCR | 1.7 |
| TNF-α | 4.3 |
| VCAM-1/CD106 | 1.6 |
| VEGF | 0.3 |
| WISP-1/CCN4 | 3.0 |

TABLE 4

List of 200 factors participating in the antibody array screen performed with plasma from mice receiving immune-checkpoint inhibitor (anti-PD-1 or anti-PD-L1) therapy Quantibody Mouse Cytokine Array (RayBiotech; Cat no: QAM-CAA-4000)

4-1BB (TNFRSF9/CD137); 6Ckine (CCL21); ACE; Activin A; ADAMTS1 (METH1); Adiponectin; ALK-1; Amphiregulin; ANG-3; ANGPTL3; Artemin; Axl; B7-1; BAFF R; bFGF; BLC (CXCL13); BTC; C5a; CCL28; CCL6; CD27; CD27L; CD30; CD30L; CD36; CD40; CD40L; CD48; CD6; Chemerin; Chordin; Clusterin; CRP; Cardiotrophin-1; CTLA4; CXCL16; Cystatin C; DAN; Decorin; Dkk-1; DLL4; Dtk; E-Cadherin; EDAR; EGF; Endocan; Endoglin; Eotaxin (CCL11); Eotaxin-2 (CCL24); Epigen; Epiregulin; E-selectin; Fas; Fas L; Fcg RIIB; Fetuin A; Flt-3L; Fractalkine; Galectin-1; Galectin-3; Galectin-7; Gas 1; Gas 6; G-CSF; GITR; GITR L; GM-CSF; gp130; Granzyme B; Gremlin; H60; HAI-1; HGF; HGF R; ICAM-1; INFg; IFNg R1; IGF-1; IGFBP-2; IGFBP-3; IGFBP-5; IGFBP-6; IL-1 R4; IL-10; IL-12p40; IL-12p70; IL-13; IL-15; IL-17; IL-17B; IL-17B R; IL-17E; IL-17F; IL-1a; IL-1b; IL-1ra; IL-2; IL-2 Ra; IL-20; IL-21; IL-22; IL-23; IL-28; IL-3; IL-3 Rb; IL-33; IL-4; IL-5; IL-6; IL-7; IL-7 Ra; IL-9; I-TAC (CXCL11); JAM-A; KC (CXCL1); Kremen-1; Leptin; Leptin R; Limitin; Lipocalin-2; LIX; LOX-1; L-selectin; Lungkine; Lymphotactin; MadCAM-1; Marapsin; MBL-2; MCP-1 (CCL2); MCP-5; MCSF; MDC (CCL22); Meteorin; MFG-E8; MIG (CXCL9); MIP-1a (CCL3); MIP-1b (CCL4); MIP-1g; MIP-2; MIP-3a (CCL20); MIP-3b (CCL19); MMP-10; MMP-2; MMP-3; Neprilysin; Nope; NOV; OPG; OPN; Osteoactivin; OX40 Ligand; P-Cadherin; PDGF-AA; Pentraxin 3; Periostin; Persephin; PF4 (CXCL4); PlGF-2; Progranulin; Prolactin; Pro-MMP-9; Prostasin; P-selectin; RAGE; RANTES (CCL5); Renin 1; Resistin; SCF; SDF-1a; sFRP-3; Shh-N; SLAM; TACI; TARC (CCL17); TCA-3; TCK-1 (CXCL7); TECK (CCL25); Testican 3; TGFb1; TIM-1; TNF RI; TNF RII; TNFa; TPO; TRAIL; TRANCE; TREM-1; TREML1; TROY; Tryptase epsilon; TSLP; TWEAK; TWEAK R; VACM-1; VEGF; VEGF R1; VEGF R2; VEGF R3; VEGF-B; VEGF-D

TABLE 5

Summary of fold changes in the levels of circulating factors in anti-PD-L1-treated vs control BALB/c and C57bl/6 mice

| | Fold change (anti-PD-L1 vs IgG) | | | |
|---|---|---|---|---|
| | BALB/c | | C57bl/6 | |
| | Female | Male | Female | Male |
| ADAMTS1 | 1.6 | 0.5 | 2.1 | 1.9 |
| ALK-1 | 2.3 | 1.5 | 6.0 | 0.6 |
| Amphiregulin | 2.7 | 2.8 | 3.0 | 0.9 |
| Axl | 2.7 | 2.2 | 2.3 | 1.9 |
| CD30 | 2.4 | 2.3 | 1.5 | 1.5 |
| Dkk-1 | 1.5 | 0.8 | 1.4 | 0.4 |
| EGF | 6.3 | 4.1 | 0.7 | 4.0 |
| Eotaxin-2 | 1.8 | 1.7 | 1.0 | 0.8 |
| Epiregulin | 2.7 | 0.6 | 0.4 | 0.2 |
| Fcg RIIB | 2.3 | 1.5 | 1.4 | 0.9 |
| Fractalkine | 2.7 | 2.0 | 1.0 | 1.0 |
| G-CSF | 2.2 | 2.7 | 2.0 | 1.2 |
| GITR L | 8.2 | 7.4 | 1.4 | 0.3 |
| Granzyme B | 2.0 | 1.1 | 2.7 | 0.7 |
| HGF | 2.3 | 0.6 | 3.7 | 3.6 |
| HGF R | 10.4 | 1.7 | 24.9 | 2.4 |
| IL-1ra | 3.6 | 1.8 | 2.9 | 1.3 |
| IL-33 | 1.3 | 2.2 | 1.6 | 1.0 |
| IL-6 | 1.8 | 1.7 | 1.0 | 0.5 |
| IL-7 | 1.7 | 1.6 | 1.1 | 0.0 |
| I-TAC | 6.1 | 7.4 | 4.2 | 1.1 |
| Lipocalin-2 | 2.0 | 4.8 | 2.6 | 2.1 |
| MadCAM-1 | 0.8 | 7.1 | 2.6 | 2.4 |
| MCP-5 | 2.2 | 4.5 | 1.3 | 1.2 |
| MDC | 2.2 | 1.8 | 0.9 | 0.6 |
| Meteorin | 0.6 | 0.7 | 1.9 | 3.0 |
| MFG-E8 | 1.8 | 2.6 | 4.3 | 1.8 |
| MIG | 1.6 | 1.2 | 1.9 | 1.4 |
| MIP-3b | 1.5 | 2.8 | 1.7 | 0.9 |
| OPG | 0.8 | 0.9 | 1.7 | 2.2 |
| Osteoactivin | 0.8 | 1.2 | 2.5 | 2.4 |
| P-Cadherin | 0.8 | 0.9 | 1.7 | 2.1 |
| Pentraxin 3 | 1.3 | 1.6 | 3.0 | 2.7 |
| Pro-MMP-9 | 3.0 | 2.2 | 1.1 | 1.3 |
| SCF | 2.6 | 3.3 | 4.5 | 3.4 |
| TACI | 2.7 | 2.9 | 2.3 | 1.3 |
| TARC | 1.4 | 1.6 | 1.5 | 0.5 |
| TNF RII | 1.3 | 2.0 | 1.6 | 2.6 |
| TREM-1 | 2.8 | 1.9 | 7.2 | 3.1 |
| TROY | 2.3 | 1.7 | 6.7 | 6.1 |
| VEGF R1 | 1.9 | 1.3 | 1.8 | 0.3 |

TABLE 6

Summary of fold changes in the levels of circulating factors in anti-PD1-treated vs control BALB/c and SCID mice

| | Fold change (anti-PD-1 vs IgG) | |
|---|---|---|
| | BALB/c | SCID |
| ADAMTS1 | 2.4 | 0.3 |
| ALK-1 | 3.4 | 3.4 |
| Amphiregulin | 3.7 | 0.0 |
| CD40L | 3.6 | 0.9 |
| Dkk-1 | 2.0 | 0.8 |
| Epigen | 2.3 | 1.8 |
| IL-17B | 3.4 | 0.3 |
| IL-17B R | 2.1 | 0.9 |
| IL-1ra | 8.7 | 1.5 |
| IL-21 | 2.6 | 1.0 |
| IL-22 | 9.1 | 0.0 |
| IL-6 | 2.1 | 1.8 |
| I-TAC | 9.3 | 1.1 |
| MFG-E8 | 2.8 | 0.6 |
| Osteoactivin | 2.5 | 2.0 |
| SCF | 2.0 | 0.0 |
| TARC | 1.5 | 0.9 |
| TREM-1 | 3.9 | 0.3 |
| TROY | 1.7 | 0.7 |
| VEGF R1 | 2.6 | 0.8 |

REFERENCES

Beyar-Katz O, Magidey K, Ben-Tsedek N, Alishekevitz D, Timaner M, Miller V, Lindzen M, Yarden Y, Avivi I, Shaked Y. Bortezomib-induced proinflammatory macrophages as a potential factor limiting anti-tumour efficacy. J Pathol. 2016 Vol. 239, Issue 3. Version on line: 29 Apr. 2016/DOI:10.1002/path.4723.

De Henau O, Rausch M, Winkler D, Campesato L F, Liu C, Cymerman D H, Budhu S, Ghosh A, Pink M, Tchaicha J, Douglas M, Tibbitts T, Sharma S, Proctor J, Kosmider N, White K, Stern H, Soglia J, Adams J, Palombella V J, McGovern K, Kutok J L, Wolchok J D, Merghoub T. Overcoming resistance to checkpoint blockade therapy by targeting PI3Kgamma in myeloid cells. Nature. 2016; 539(7629):443-7.

De Palma M, Lewis C E. Macrophage regulation of tumor responses to anticancer therapies. Cancer Cell. 2013; 23(3):277-86.

Duraiswamy J, Kaluza K M, Freeman G J, Coukos G. Dual blockade of PD-1 and CTLA-4 combined with tumor vaccine effectively restores T-cell rejection function in tumors. Cancer Res. 2013; 73(12):3591-603.

Gajewski T F, Schreiber H, Fu Y X. Innate and adaptive immune cells in the tumor microenvironment. Nat Immunol. 2013; 14(10):1014-22.

Katz O B, Shaked Y. Host effects contributing to cancer therapy resistance. Drug Resist Updat. 2015; 19:33-42.

Kim K H, Sederstrom J M. Assaying Cell Cycle Status Using Flow Cytometry. Current protocols in molecular biology. 2015; 111:28 6 1-11.

Kim J, Denu R A, Dollar B A, Escalante L E, Kuether J P, Callander N S, Asimakopoulos F, Hematti P. Macrophages and mesenchymal stromal cells support survival and proliferation of multiple myeloma cells. British Journal of Haematology. 2012; 158(3):336-46.

Kodumudi K N, Siegel J, Weber A M, Scott E, Sarnaik A A, Pilon-Thomas S. Immune Checkpoint Blockade to Improve Tumor Infiltrating Lymphocytes for Adoptive Cell Therapy. PLoS one. 2016; 11(4):e0153053.

Ma Y, Adjemian S, Mattarollo S R, Yamazaki T, Aymeric L, Yang H, Portela Catani J P, Hannani D, Duret H, Steegh K, Martins I, Schlemmer F, Michaud M, Kepp O, Sukkurwala A Q, Menger L, Vacchelli E, Droin N, Galluzzi L, Krzysiek R, Gordon S, Taylor P R, Van Endert P, Solary E, Smyth M J, Zitvogel L, Kroemer G. Anticancer chemotherapy-induced intratumoral recruitment and differentiation of antigen-presenting cells. Immunity. 2013; 38(4):729-41.

Makkouk A, Weiner G J. Cancer immunotherapy and breaking immune tolerance: new approaches to an old challenge. Cancer Res. 2015; 75(1):5-10.

Ostrand-Rosenberg S, Sinha P. Myeloid-derived suppressor cells: linking inflammation and cancer. Journal of Immunology. 2009; 182(8):4499-506.

Pardoll D M. The blockade of immune checkpoints in cancer immunotherapy. Nature reviews Cancer. 2012; 12(4):252-64.

Postow M A, Callahan M K, Wolchok J D. Immune Checkpoint Blockade in Cancer Therapy. J Clin Oncol. 2015; 33(17):1974-82.

Romano E, Romero P. The therapeutic promise of disrupting the PD-1/PD-L1 immune checkpoint in cancer: unleashing the CD8 T cell mediated anti-tumor activity results in significant, unprecedented clinical efficacy in various solid tumors. J Immunother Cancer. 2015; 3:15.

Sato T, Terai M, Tamura Y, Alexeev V, Mastrangelo M J, Selvan S R. Interleukin 10 in the tumor microenvironment: a target for anticancer immunotherapy. Immunol Res. 2011; 51 (2-3): 170-82.

Shaked Y. Balancing efficacy of and host immune responses to cancer therapy: the yin and yang effects. Nat Rev Clin Oncol. 2016.

Shaked Y, Ciarrocchi A, Franco M, Lee C R, Man S, Cheung A M, Hicklin D J, Chaplin D, Foster F S, Benezra R, Kerbel R S. Therapy-induced acute recruitment of circulating endothelial progenitor cells to tumors. Science. 2006; 313(5794):1785-7.

Shaked Y, Henke E, Roodhart J M, Mancuso P, Langenberg M H, Colleoni M, Daenen L G, Man S, Xu P, Emmenegger U, Tang T, Zhu Z, Witte L, Strieter R M, Bertolini F, Voest E E, Benezra R, Kerbel R S. Rapid chemotherapy-induced acute endothelial progenitor cell mobilization: implications for antiangiogenic drugs as chemosensitizing agents. Cancer Cell. 2008; 14(3):263-73.

Sharma P, Hu-Lieskovan S, Wargo J A, Ribas A. Primary, Adaptive, and Acquired Resistance to Cancer Immunotherapy. Cell. 2017; 168(4):707-23.

Swart M, Verbrugge I, Beltman J B. Combination Approaches with Immune-Checkpoint Blockade in Cancer Therapy. Frontiers in Oncology. 2016; 6:233.

Topalian S L, Drake C G, Pardoll D M. Immune checkpoint blockade: a common denominator approach to Cancer Immunotherapy. Cancer Cell 2015; 27(4): 450-61.

What is claimed is:

1. A method for predicting the response of a non-small cell lung cancer (NSCLC) patient to treatment with an immune checkpoint inhibitor (ICI), the method comprising the steps of:
   (i) administering said ICI to said cancer patient, wherein said ICI is selected from anti-PD-1 treatment and anti-PD-L1 treatment;
   (ii) performing an assay on a biological sample selected from blood plasma, whole blood, blood serum or peripheral blood mononuclear cells obtained from the cancer patient at a time period after said administering said ICI, to determine the levels of one or more of a plurality of factors selected from 6Ckine, IL-18, Amphiregulin, IL-2R, FGF-7, Activin A, IFN-gamma, IL-17, Follistatin, IL-20, IL-17C, SCF, TSLP, VEGFC, IL-1A, IL-11, MIP-1a, TACI, IL-15, BRAK, LIF, IL-5, TGF-B3, IL-1B, angiopoietin-2, IL-13R1, MIG, IL-27, VEGFR3, PF4, LRP6, IL-13, PARC, IL-31, IL-23, GM-CSF, IL-3, Tie2, TGF-B2, IL-12, TGF-B1, IL-17F, IL-17R, MCP-1, IL-3RA, MCP-3, HCC-4, Eotaxin-3, G-CSF, MCP-3, and ADAMTS1;
   (iii) obtaining reference levels for each of the one or more of the plurality of factors of step (ii) in a biological sample obtained from the lung cancer patient before said administering the ICI; and
   (iv) determining said NSCLC patient's responsiveness to the treatment with said ICI, wherein an increase in levels of said one or more of the plurality of factors in said biological sample obtained from the NSCLC patient at a time period after said administering said ICI as compared to said reference level indicates a NSCLC patient with reduced responsiveness to said treatment with said ICI.

2. The method of claim 1, wherein the biological sample of steps (ii) and (iii) is blood plasma.

3. The method of claim 1, wherein said administering the ICI is the first session of treatment with said ICI, the biological sample of step (ii) is obtained from the cancer patient at about 20 hours or more after said first session of treatment, and the reference biological sample of step (iii) is obtained from the cancer patient at a time point of at about 72 hours or less before said first session of treatment with the ICI.

4. The method of claim 1, wherein said administering the ICI is one of multiple sessions of treatment that is not the first session of treatment with the ICI, and the biological sample is obtained from the cancer patient at any time point between two consecutive sessions of treatment with the ICI, wherein said biological sample is simultaneously the biological sample of step (ii) and the reference biological sample according to step (iii) for a next session assay according to step (ii).

5. The method of claim 4, wherein the time between two consecutive sessions of treatment is 2 or 3 weeks, and the biological sample is obtained at day 1 to 21 days after the session of treatment that is not the first session of treatment with the ICI.

6. The method of claim 1, wherein the increase established in step (iv) is defined by a fold change of ≥1.5 indicating upregulation in the level of each of the one or more of the plurality of factors, these values being considered predictive of reduced responsiveness of the cancer patient to the treatment with the said ICI.

7. The method of claim 1, wherein the prediction of reduced responsiveness of the cancer patient to the treatment with the ICI is based on statistically significant fold changes of the induced factors.

8. The method of claim 1, wherein the ICI is a monoclonal antibody selected from an anti-PD-1, and an anti-PD-L1 antibody.

9. The method of claim 8, wherein the anti-PD-1 monoclonal antibody is Pembrolizumab, Nivolumab, Pidilizumab, Cemiplimab, AMP-224, MEDI0680, or Spartalizumab.

10. The method of claim 8, wherein the anti-PD-L1 monoclonal antibody is Atezolizumab, Avelumab, Durvalumab or MDX-1105.

11. The method of claim 1, wherein the cancer patient is treated with a combination of two ICIs.

12. The method of claim 11, wherein said combination of two ICIs is selected from: Nivolumab (anti-PD-1) and Atezolimumab (anti-PD-L1); Durvalumab (anti-PD-L1) and Pembrolizumab (anti-PD-1); nivolumab and ipilimumab (anti-CTLA4) and any combination thereof.

13. The method of claim 1, wherein the ICI is in combination with an agonistic monoclonal antibody against T-cell co-stimulatory molecules.

14. The method of claim 13, wherein the ICI is Nivolumab (anti-PD-1) and the agonistic monoclonal antibody is Urelumab (anti-4-IBB).

15. The method of claim 1, wherein the ICI is administered in combination with one or more conventional cancer therapy.

16. A method of increasing an anticancer effect of an immune checkpoint inhibitor (ICI) in a cancer patient, the method comprising the steps of:
   (i) performing an assay on a biological sample selected from blood plasma, whole blood, blood serum or peripheral blood mononuclear cells obtained from the cancer patient at a time period after a session of treatment with said ICI, to determine the levels of amphiregulin in the circulation of said cancer patient in response to treatment with said ICI, wherein said ICI is anti-PD1 treatment or anti-PD-L1 treatment;
   (ii) obtaining reference levels for amphiregulin in a biological sample selected from blood plasma, whole blood, blood serum or peripheral blood mononuclear cells, obtained from the cancer patient before said session of treatment with the ICI; and
   (iii) for a cancer patient with increased levels of amphiregulin in said biological sample obtained from the cancer patient at a time period after a session of treatment with said ICI as compared to said reference levels, treating the cancer patient with the ICI in combination with an anti-amphiregulin antibody, thereby increasing an anticancer effect of an ICI.

17. The method of claim 16, wherein said anti-amphiregulin antibody is AF989.

18. The method of claim 16, wherein the biological samples of step (i) and step (ii) are both blood plasma.

19. The method of claim 16, wherein said session of treatment with the ICI is the first session of treatment with said ICI, the biological sample of step (i) is obtained from the cancer patient at about 20 hours or more after said first session of treatment, and the reference biological sample of step (ii) is obtained from the cancer patient at a time point about 72 hours or less before said first session of treatment with the ICI or wherein said session of treatment with the ICI is one of multiple sessions of treatment that is not the first session of treatment with the ICI, and the biological sample is obtained from the cancer patient at any time point between two consecutive sessions of treatment, wherein said biological sample is simultaneously the biological sample of step (i) and the reference biological sample according to step (ii) for a next session assay according to step (i).

20. The method of claim 19, wherein the time between two consecutive sessions of treatment is 2 or 3 weeks, and the biological sample is obtained at day 1 to 21 days after the session of treatment that is not the first session of treatment with the ICI.

21. The method of claim 16, wherein the increased levels established in step (iii) is defined by a fold change of ≥1.5, this value being considered predictive of a need to treat the patient with the ICI in combination with the anti-amphiregulin antibody.

22. The method of claim 7, wherein said plurality of factors is selected from: 6Ckine, IL-18, IL-17C, IL-5, IL-27, angiopoietin-2, IL-12, IL-23, and IL-2R.

* * * * *